(12) United States Patent
Tarlow et al.

(10) Patent No.: US 9,675,788 B2
(45) Date of Patent: *Jun. 13, 2017

(54) HANDHELD TOPICAL APPLICATOR

(71) Applicant: Golf Rite Products, LLC, Santa Barbara, CA (US)

(72) Inventors: Kenneth M. Tarlow, Santa Barbara, CA (US); Frank Francavilla, Wantage, NJ (US)

(73) Assignee: Golf Rite Products, LLC, Santa Barbara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/090,481

(22) Filed: Apr. 4, 2016

(65) Prior Publication Data

US 2016/0220799 A1 Aug. 4, 2016

Related U.S. Application Data

(63) Continuation-in-part of application No. 14/058,212, filed on Oct. 18, 2013, now Pat. No. 9,327,545.
(Continued)

(51) Int. Cl.
*B43K 23/00* (2006.01)
*A61M 35/00* (2006.01)
(Continued)

(52) U.S. Cl.
CPC ......... *A61M 35/003* (2013.01); *B43K 23/008* (2013.01); *B43K 23/12* (2013.01); *B43K 27/08* (2013.01); *B43K 29/005* (2013.01)

(58) Field of Classification Search
CPC ........ B43K 3/04; B43K 23/00; B43K 23/008; B43K 23/06; B43K 27/00; B43K 27/08; B43K 31/00
(Continued)

(56) References Cited

U.S. PATENT DOCUMENTS 3,003,183 A 10/1961 Rosenthal
3,019,762 A 2/1962 Haufz
(Continued)

FOREIGN PATENT DOCUMENTS

AU 5584186 9/1986
AU 200141985 9/2001
(Continued)

OTHER PUBLICATIONS

The International Searching Authority, PCT International Search Report, Jan. 12, 2015, 11 pages.
(Continued)

*Primary Examiner* — Jennifer C Chiang
*Assistant Examiner* — Bradley Oliver
(74) *Attorney, Agent, or Firm* — Hankin Patent Law, APC; Marc E. Hankin; Anooj Patel

(57) ABSTRACT

A handheld topical applicator. The handheld topical applicator is preferably adapted to release a precise amount of liquid onto a surface and is preferably used for various applications such as marking a surface and/or providing a proper amount of dosage for medicinal applications. The handheld topical applicator may comprise a liquid delivery system for dispensing a precise amount of liquid onto various surfaces, a projecting/retracting mechanism, and an audible and/or tactile physical feedback mechanism. The projecting/retracting mechanism may controllably retract or protrude a nib into and out of the housing, and the audible/physical feedback mechanism may provide either a physical and/or audible click once a desired amount of liquid transfers onto the surface.

20 Claims, 19 Drawing Sheets

Related U.S. Application Data

(60) Provisional application No. 61/718,881, filed on Oct. 26, 2012.

(51) Int. Cl.
  B43K 23/008 (2006.01)
  B43K 23/12 (2006.01)
  B43K 27/08 (2006.01)
  B43K 29/00 (2006.01)

(58) Field of Classification Search
  USPC ...... 401/17, 23, 99, 103, 194, 196, 202, 206
  See application file for complete search history.

(56) References Cited

U.S. PATENT DOCUMENTS

| | | |
|---|---|---|
| 4,685,820 A | 8/1987 | Kremer |
| 4,792,252 A | 12/1988 | Kremer |
| 5,582,598 A | 12/1996 | Chanoch |
| 5,971,648 A | 10/1999 | Koreska |
| D438,903 S | 3/2001 | Rosenbaum |
| 6,361,234 B1 | 3/2002 | Rukan |
| 6,379,271 B1 | 4/2002 | Arnke |
| D483,408 S | 12/2003 | Smiskol |
| 6,932,794 B2 | 8/2005 | Gambattista |
| 6,986,760 B2 | 1/2006 | Giambattista |
| 7,210,869 B2 | 5/2007 | Kageyama |
| 7,556,615 B2 | 7/2009 | Pettis |
| 7,713,229 B2 | 5/2010 | Veit |
| 7,927,281 B2 | 4/2011 | Wheeler |
| 7,959,368 B2 | 6/2011 | Sheu et al. |
| 8,092,108 B2 | 1/2012 | Bainbridge |
| 2004/0162524 A1 | 8/2004 | Schiff |
| 2008/0015511 A1 | 1/2008 | Veasey |
| 2009/0069752 A1 | 3/2009 | Raj |
| 2009/0069753 A1 | 3/2009 | Ruan |
| 2009/0275915 A1 | 11/2009 | Harms |
| 2010/0170409 A1 | 7/2010 | Chan |
| 2010/0186739 A1 | 7/2010 | Kronestedt |
| 2010/0239357 A1 | 9/2010 | Bolton |
| 2010/0296858 A1 | 11/2010 | Richards |
| 2011/0071492 A1 | 3/2011 | Horvath |
| 2011/0092917 A1 | 4/2011 | Wei |
| 2011/0118667 A1 | 5/2011 | Zaiken |
| 2011/0158738 A1 | 6/2011 | Bainbridge |
| 2011/0257604 A1 | 10/2011 | Banik |
| 2013/0243514 A1 | 9/2013 | Ballot |

FOREIGN PATENT DOCUMENTS

| | | |
|---|---|---|
| BR | 0109111 | 6/2003 |
| CA | 2402333 | 11/2007 |
| CA | 2867154 | 9/2013 |
| CN | 1427681 | 7/2003 |
| CN | 1225369 | 11/2005 |
| DE | 3681317 | 10/1991 |
| DE | 60140861 | 2/2010 |
| EP | 0197281 | 10/1987 |
| EP | 1261261 | 12/2002 |
| JP | 2003525775 | 9/2003 |
| JP | 4131794 | 8/2008 |
| MX | PA02008713 | 4/2003 |
| TW | 548202 | 8/2003 |
| WO | 8605144 | 9/1986 |
| WO | 0165970 | 12/2001 |
| WO | 2013138664 | 9/2013 |

OTHER PUBLICATIONS

MIMLD816, Inkavote Demonstration, Demonstration Video, Nov. 4, 2008 http://www.youtube.com/watch?v=1HH4bZtWqUE.
Inkavote Procedures, Use Manual, Nov. 1, 2010 http://www.sos.ca.gov/voting-systems/vendors/use-procedures/los-angeles-use-procedures-complete.pdf.
Camelot Pen http://www.goto-promo.com/products/1212/123081/camelot-pen-184172.html.
Dymo Pen http://www.goto-promo.com/products/1212/123081/dymo-pen-185183.html.
Noel Runyan, Jim Tobias, InkaVote Plus Voting System Access Review, Access Report, Jan. 2, 2008 https://www.sos.ca.gov/voting-systems/oversight/ttbr/inkavote-access-report.pdf.

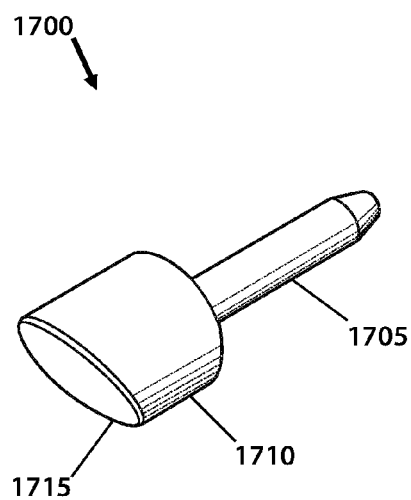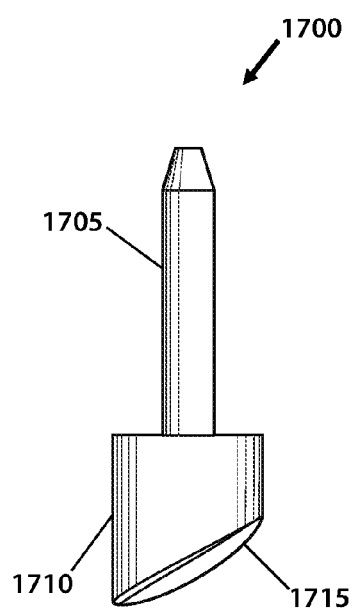
Fig. 17a
Fig. 17b

HANDHELD TOPICAL APPLICATOR

CROSS-REFERENCE TO RELATED APPLICATIONS

This Application is a continuation-in-part of U.S. Non-Provisional patent application Ser. No. 14/058,212, filed on Oct. 18, 2013, titled "Handheld Precise Liquid Marker", by co-inventors Kenneth M. Tarlow and Frank Francavilla, the contents of which are expressly incorporated herein by this reference as though set forth in their entirety, and to which priority is claimed. U.S. Non-Provisional patent application Ser. No. 14/058,212 claims the benefit of U.S. Provisional Patent Application No. 61/718,881, filed on Oct. 26, 2012, titled "Handheld Precise Liquid Marker", by inventor Kenneth Martin Tarlow, the contents of which are expressly incorporated herein by this reference as though set forth in their entirety.

FIELD OF USE

This present disclosure relates generally to topical applicators, and more particularly, to handheld topical application devices with a delivery system for releasing a precise amount of liquid, such as medicinal liquid, when marking or dosing a surface while, at the same time, providing tactile or audible feedback.

BACKGROUND

Various topical products in the form of liquids, creams, ointments, and gels currently exist. These topical products are generally used for the treatment of muscle aches, pain, and skin disorders and typically must be applied on the skin adequately with the proper dosage amount in order to have a substantial effect. This in turn typically requires that the dosage be measured prior to application onto the affected area of the skin.

The process of administering topical medication, however, may cause the user to unintentionally deliver an over-dosage or under-dosage amount, resulting with an undesirable application of the liquid. Additionally, conventional topical applicators fail to provide any audible or physical feedback to notify the user that a sufficient amount of liquid is applied. The use of an audible or physical feedback is especially helpful to prevent the unnecessary release of liquid onto the affected surface. Otherwise, without any feedback or notification mechanism, the user might apply more or less liquid than necessary, thereby resulting with an improper treatment.

Therefore, there is a need for a topical applicator device with a new and improved liquid delivery mechanism that will release a precise amount of topical liquid onto a surface such as a skin. Preferably, the liquid delivery mechanism of the device also provides some audible and/or physical feedback to the user when an appropriate amount of liquid has been released.

SUMMARY OF ILLUSTRATIVE EMBODIMENTS

To minimize the limitations in the prior art, and to minimize other limitations that will become apparent upon reading and understanding the present specification, the following discloses a handheld topical applicator with a delivery system that releases a precise amount of liquid (e.g., medicinal liquids) onto a surface. The liquid delivery mechanism preferably utilizes an audible and/or physical feedback and is preferably used in various applications such as medicinal applications.

One embodiment may be a handheld topical applicator, comprising: a front housing; a first nib; a piston; a biasing member; and a reservoir; wherein the front housing may contain the reservoir; wherein the reservoir may be adapted to store a liquid; wherein the first nib may be coupled to a proximal end of the front housing and may be adapted to be in fluid communication with the liquid stored in the reservoir; wherein the piston may be positioned at a distal end of the front housing; wherein the biasing member may be disposed inside the piston, such that the piston is adapted to bias towards the distal end of the front housing; wherein the piston may comprise: a first cylinder, a second cylinder, one or more first tabs, and one or more second tabs; wherein the one or more first tabs may be disposed at an outer surface of the first cylinder; wherein the one or more second tabs may be disposed at an inner surface of the second cylinder; and wherein the one or more first tabs and the one or more second tabs may be adapted to produce an audible click after a user applies pressure to the first nib against a surface, such that the applied pressure causes the one or more first tabs to contact the one or more second tabs. The handheld topical applicator may further comprise: a main housing; wherein the main housing may comprise a central opening; wherein the main housing may substantially enclose the front housing, such that, at least a portion of the first nib protrudes through the central opening of the main housing and controllably retracts through the central opening of the main housing upon the applied pressure of the first nib onto a surface; wherein the front housing may comprise a shoulder located at an exterior of the front housing; wherein the main housing may comprise an inner flange located inside an interior of the main housing; and wherein the shoulder may be adapted to restrict the projection of the at least the portion of the first nib through the central opening of the main housing when the shoulder of the front housing contacts the inner flange of the main housing. The one or more first tabs and one or more second tabs may produce a tactile response upon receiving the applied pressure to the first nib. The first nib may be one of a plurality of nibs; and wherein the first nib may be adapted to be replaced with one or more different nibs of the plurality of nibs. The plurality of nibs may have different porosity densities, such that the handheld topical applicator is adjustable for one or more different applications. The one or more of the plurality of nibs may be constructed of an anti-microbial material. The liquid stored in the reservoir may be limited to an amount for a single use application, such that the handheld topical applicator is a single use device. The main housing may comprise a window indicator positioned outside the reservoir to show an amount of the liquid stored in the reservoir. The front housing may be constructed of a transparent material. The first nib may be adapted to change color based on an amount of the liquid stored in the reservoir. The first nib may be adapted to release a predetermined amount of liquid when the first nib is applied against a surface based on a flow rate; wherein the flow rate may be based on a material density of the reservoir and a porosity of the first nib.

Another embodiment may be a handheld topical applicator, comprising: a front housing; a first nib; a piston; a biasing member; and a reservoir; wherein the front housing may contain the reservoir; wherein the reservoir may be adapted to store a liquid; wherein the first nib may be coupled to a proximal end of the front housing and may be adapted to be in fluid communication with the liquid stored in the reservoir; wherein the piston may be positioned at a distal end of the front housing; wherein the biasing member may be disposed within the piston, such that the piston is adapted to bias towards the distal end of the front housing; wherein the piston may comprise: a first cylinder, a second cylinder, one or more first tabs, and one or more second tabs; wherein the one or more first tabs may be disposed at an outer surface of the first cylinder; wherein the one or more second tabs may be disposed at an inner surface of the second cylinder; and wherein the one or more first tabs and the one or more second tabs may be adapted to produce an audible click after a user applies a pressure to the first nib against a surface for a predetermined amount of time, such that the applied pressure of the first nib against the surface causes the one or more first tabs to contact the one or more second tabs. The handheld topical applicator may further comprise: a main housing; wherein the main housing may comprise a central opening; wherein the main housing may substantially enclose the front housing, such that, at least a portion of the first nib protrudes through the central opening of the main housing and controllably retracts through the central opening of the main housing upon compression of the first nib onto a surface; wherein the front housing may comprise a shoulder located at an exterior of the front housing; wherein the main housing may comprise an inner flange located inside an interior of the main housing; and wherein the shoulder may be adapted to restrict the projection of the portion of the first nib through the central opening of the main housing when the shoulder of the front housing contacts the inner flange of the main housing. The one or more first tabs and one or more second tabs may produce a tactile response upon receiving the applied pressure to the first nib. The first nib may be one of a plurality of nibs; and wherein the first nib may be adapted to be replaced with one or more different nibs of the plurality of nibs. The one or more different nibs may have different porosity densities, such that the handheld topical applicator is used for one or more different applications. The main housing may comprise a window indicator positioned outside the reservoir; wherein the window indicator may show an amount of the liquid stored in the reservoir. The front housing may be constructed of a transparent material. The first nib may be adapted to change color based on an amount of the liquid stored in the reservoir. The first nib may be adapted to release a predetermined amount of liquid when the first nib is applied against a surface based on a flow rate; and wherein the flow rate may be based on a material density of the reservoir and a porosity of the first nib.

Another embodiment may be a handheld topical applicator, comprising: a front housing; a first nib; a piston; a biasing member; and a first reservoir; wherein the front housing may contain the first reservoir; wherein the first reservoir may be adapted to store a liquid; wherein the front housing may have a proximal end and a distal end; wherein the first nib may be positioned at the proximal end of the front housing and may be in fluid communication with the first reservoir; wherein the piston may be positioned behind the distal end of the front housing; and wherein the biasing member may be disposed inside the piston, such that the piston biases towards the distal end of the front housing. The handheld topical applicator may further comprise: a main housing; wherein the main housing may have a central opening; and wherein the front housing may be substantially enclosed within the main housing, such that, a portion of the first nib may protrude through the central opening of the main housing, and, such that a portion of the first nib may controllably retract through the central opening of the main housing upon compression of the first nib onto one or more surfaces. The front housing may comprise a shoulder located at an exterior of the front housing; wherein the main housing may comprise an inner flange located inside an interior of the main housing; and wherein the shoulder may be adapted to restrict the projection of the portion of the nib through the central opening of the main housing when the shoulder of the front housing contacts the inner flange of the main housing. The piston may comprise: a first cylinder, a second cylinder, one or more first tabs, and one or more second tabs; wherein the one or more first tabs may be located at an outer surface of the first cylinder; wherein the one or more second tabs may be located at an inner surface of the second cylinder; wherein the biasing member may be positioned in-between the first cylinder and the second cylinder, such that a portion of the second cylinder may overlap a portion of the first cylinder; and wherein the one or more first tabs and one or more second tabs may produce an audible click upon the compression of the first nib, such that the compression of the first nib may cause the one or more first tabs to contact the one or more second tabs. The one or more first tabs and one or more second tabs may produce a tactile response upon the compression of the first nib. The first nib may be substantially curved. The handheld topical applicator may further comprise: a rear housing; a second nib; and a second reservoir; wherein the rear housing may be adapted to hold the second reservoir; wherein the second reservoir may be configured to store the liquid; wherein the second reservoir may have a proximal end and a distal end; and wherein the second nib may be positioned at the rear end of the second reservoir and may be in fluid communication with the second reservoir. The handheld topical applicator may further comprise a plug; wherein the plug may removeably attach to the proximal end of the rear housing; and wherein the piston may be configured to removeably attach to the plug. The second nib may comprise a substantially sharp point, such that the second nib is configured to produce one or more thin strokes on the one or more surfaces when the second nib is applied to the one or more surfaces. The main housing may comprise a grip; and wherein the grip may be substantially curved and may comprise a plurality of dimples.

Another embodiment may be a handheld topical applicator, comprising: a front housing; a first nib; a piston; a biasing member; a main housing; and a first reservoir; wherein the front housing may contain the first reservoir; wherein the first reservoir may be adapted to store a liquid; wherein the front housing may have a proximal end and a distal end; wherein the first nib may be positioned at the proximal end of the front housing and may be in fluid communication with the first reservoir; wherein the piston may be positioned behind the distal end of the front housing; wherein the biasing member may be disposed inside the piston, such that the piston biases towards the distal end of the front housing; wherein the main housing comprises a central opening; wherein the front housing may be substantially enclosed within the main housing, such that, a portion of the first nib protrudes through the central opening of the main housing, and, such that a portion of the first nib controllably retracts through the central opening of the main housing upon compression of the first nib onto one or more surfaces; and wherein the first nib may be substantially curved; wherein the piston may comprise: a first cylinder, a second cylinder, one or more first tabs, and one or more second tabs; wherein the one or more first tabs may be located at an outer surface of the first cylinder; wherein the one or more second tabs may be located at an inner surface of the second cylinder; wherein the biasing member may be positioned between the first cylinder and the second cylinder, such that a portion of the second cylinder overlaps a portion of the first cylinder; and wherein the one or more first tabs and one or more second tabs produces an audible click upon the compression of the first nib, such that the compression of the first nib causes the one or more first tabs to contact the one or more second tabs. The front housing may further comprise a shoulder; wherein the shoulder of the front housing may be located at an exterior of the front housing; wherein the main housing may comprise an inner flange located inside an interior of the main housing; and wherein the shoulder may be configured to restrict the projection of the portion of the nib through the central opening of the main housing when the shoulder of the front housing contacts the inner flange of the main housing. The one or more first tabs and one or more second tabs may produce a tactile response upon the compression of the first nib. The handheld topical applicator may further comprise: a rear housing; a second nib; and a second reservoir; wherein the rear housing may be adapted to hold the second reservoir; wherein the second reservoir may be adapted to store the liquid; wherein the second reservoir may have a proximal end and a distal end; and wherein the second nib may be positioned at the distal end of the second reservoir and may be in fluid communication with the second reservoir. The handheld topical applicator may further comprise a plug; wherein the plug may removeably attach to the proximal end of the rear housing; and wherein the piston may be configured to removeably attach to the plug. The second nib may have a substantially sharp point, such that the second nib may be configured to create one or more thin strokes on the one or more surfaces when the second nib is applied to the one or more surfaces. The main housing may comprise a grip; and wherein the grip may be substantially curved and may comprise a plurality of dimples. The first nib may be constructed of a porous polymer material. The second nib may be constructed of a porous polymer material.

Another embodiment may be a handheld topical applicator, comprising: a front housing; a first nib; a piston; a biasing member; a main housing; a rear housing; a second nib; a plug; a first reservoir; and a second reservoir; wherein the front housing may contain the first reservoir; wherein the first reservoir may be adapted to store a liquid; wherein the front housing may have a proximal end and a distal end; wherein the first nib may be positioned at the proximal end of the front housing and may be in fluid communication with the first reservoir; wherein the piston may be positioned behind the distal end of the front housing; wherein the biasing member may be disposed inside the piston, such that the piston biases towards the distal end of the front housing; wherein the main housing may comprise a central opening; wherein the front housing may be substantially enclosed within the main housing, such that, a portion of the first nib protrudes through the central opening of the main housing, and, such that a portion of the first nib controllably retracts through the central opening of the main housing upon compression of the first nib onto one or more surfaces; wherein the front housing may further comprise a shoulder; wherein the shoulder may be located at an exterior of the front housing; wherein the main housing may comprise an inner flange located inside an interior of the main housing; wherein the shoulder may be configured to restrict the projection of the portion of the nib through the central opening of the main housing when the shoulder of the front housing contacts the inner flange of the main housing; wherein the piston may comprise: a first cylinder, a second cylinder, one or more first tabs, and one or more second tabs; wherein the one or more first tabs may be located at an outer surface of the first cylinder; wherein the one or more second tabs may be located at an inner surface of the second cylinder; wherein the biasing member may be disposed between the first cylinder and the second cylinder, such that a portion of the second cylinder overlaps a portion of the first cylinder; wherein the one or more first tabs and one or more second tabs may be adapted to produce an audible click upon the compression of the first nib, such that the compression of the first nib causes the one or more first tabs to contact the one or more second tabs; wherein the one or more first tabs and one or more second tabs may be adapted to produce a tactile response upon the compression of the first nib; wherein the rear housing may be adapted to hold the second reservoir; wherein the second reservoir may be adapted to store the liquid; wherein the second reservoir may have a proximal end and a distal end; wherein the second nib may be positioned at the distal end of the second reservoir and may be in fluid communication with the second reservoir; wherein the plug may be adapted to removeably attach to the proximal end of the rear housing; wherein the piston may be adapted to removeably attach to the plug; wherein the second nib may have a substantially sharp point, such that the second nib may be adapted to create one or more thin strokes on the one or more surfaces when the second nib is applied to the one or more surfaces; and wherein the first nib may be constructed of a porous polymer material.

It is an object to provide a handheld topical applicator for dispensing a precise amount of liquid on a particular surface such as a skin of a human or animal.

It is an object to provide a handheld topical applicator used for various applications such as marking the surface of an object and/or applying the proper amount of dosage of topical medicine.

It is an object to provide a topical applicator for a single vertical press marking.

It is an object to provide a topical applicator adapted for interchanging various nibs.

It is an object to provide a topical applicator with a nib that provides passive control flow of a liquid onto a surface.

It is an object to provide a topical applicator with a nib that controllably retracts within the main housing of the device upon application of the nib onto a surface.

It is an object to provide a topical applicator with a housing and grip that is ergonomic.

It is an object to provide a topical applicator with a liquid delivery system that releases a sufficient amount of liquid upon application onto a surface without producing any blotches or mess.

It is an object to provide a topical applicator that produces a physical and/or audible click once a desired amount of liquid transfers onto one or more surfaces.

It is an object of the new device to overcome the limitations of the prior art.

Additional embodiments will be understood from the detailed description of illustrative embodiments.

BRIEF DESCRIPTION OF THE DRAWINGS

The drawings are of illustrative embodiments. They do not illustrate all embodiments. Other embodiments may be used in addition or instead. Details which may be apparent or unnecessary may be omitted to save space or for more effective illustration. Some embodiments may be practiced with additional components or steps and/or without all of the components or steps which are illustrated. When the same numeral appears in different drawings, it refers to the same or like components or steps.

FIGS. 17A and 17B are illustrations of another embodiment of the nib.

DETAILED DESCRIPTION OF ILLUSTRATIVE EMBODIMENTS

Figure 1:
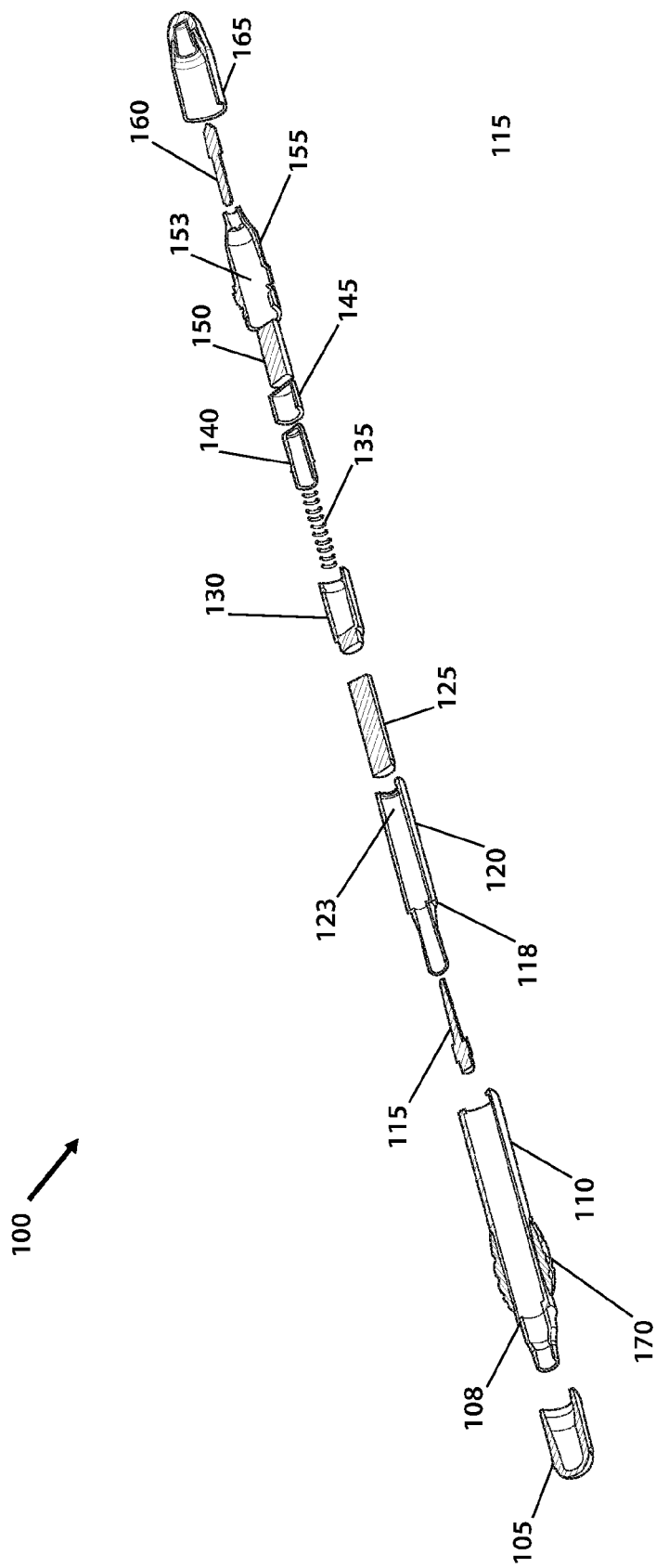
FIG. 1 is an illustration of a cross-sectional, exploded perspective view of one embodiment of the handheld topical applicator.

In the following detailed description, numerous specific details are set forth in order to provide a thorough understanding of various aspects of one or more embodiments. However, these embodiments may be practiced without some or all of these specific details. In other instances, well-known methods, procedures, and/or components have not been described in detail so as not to unnecessarily obscure aspects of the embodiments of the present disclosure.

While multiple embodiments are disclosed, other embodiments will become apparent to those skilled in the art from the following detailed description. As will be realized, these embodiments are capable of modifications in various obvious aspects. Accordingly, the screen shot figures, and the detailed descriptions thereof, are to be regarded as illustrative in nature and not restrictive. Also, the reference or non-reference to a particular embodiment shall not be interpreted to limit the scope of protection.

In the following description, certain terminology is used to describe certain features of one or more embodiments. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

As used herein, the terms "approximately" and "about" generally refer to a deviance of within 5% of the indicated number or range of numbers. In one embodiment, the term "approximately" and "about", refer to a deviance of between 1-10% from the indicated number or range of numbers.

As used herein, the term "handheld topical applicator" generally refers to any disposable or re-usable device, preferably with a liquid delivery mechanism, designed to release a precise amount of fluid such as ink, medicinal liquid, or any other liquid, and may be of any shape such as compact or pen-type. The marking of the handheld topical applicator may be provided through a mechanical (optionally manual) or stored energy drive mechanism, such as a biasing member. The marking device may include a separate liquid cartridge to hold liquid.

The terms "housing", "main housing", "front housing", and "rear housing" generally refer to an exterior housing (e.g., "body", "shell", "outer body") or interior housing ("inner body", "insert"), which may have internal and external threads. The housing may be designed to enable the safe, correct, and comfortable handling of the handheld topical applicator or any of its mechanisms. Usually, the housing is designed to house, fix, protect, guide, and/or engage with any of the inner components of the handheld topical applicator (e.g., the projecting-retracting mechanism, liquid cartridge, biasing member) by limiting the exposure to contaminants, such as liquid, dust, dirt, etc. . . . . In general, the housing may be unitary or a multi-part component of tubular or non-tubular shape. Usually, the exterior housing serves to house a reservoir from which fluid may be stored. However, the reservoir may be directly coupled to the housing, so as to be partly or fully external to the housing.

The term "piston" generally refers to a component adapted to operate through/within the housing, designed to transfer movement within the handheld topical applicator, for purposes of providing a counter force. The piston may be flexible or rigid. The piston may be a simple rod, spring-loaded system, lead-screw, rack and pinion system, or the like.

As used herein, the term "biasing member" refers to a resilient or elastic component capable of providing a force in a particular direction and/or may be capable of returning to an original shape or position after having been compressed, including without limitation, springs, return springs, coils, elastomeric materials, and the like.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

The present specification discloses a new and improved handheld topical applicator for releasing a precise amount of liquid onto a surface. The handheld topical applicator may provide multiple applications such as marking surface and/ or providing a proper amount of dosage for medicinal applications. The handheld topical applicator preferably comprises a reservoir adapted to store a liquid and may be applied to certain surfaces such as a person's skin. The liquid is preferably delivered from the reservoir and out through a nib once pressure is applied to the nib. The nib may also be adapted to retract inside the tip of the front housing and is preferably restricted by contact between the inner flange of a main housing and the shoulder of the front housing. The nib may controllably retract within the opening of the main housing due to the inner workings of the piston and tabs. A biasing member (e.g., spring) located behind the reservoir generally provides the counter force to push the nib outwards. An audible "click" may be heard once contact occurs between the tabs of the piston. The "click" generally informs the user that a sufficient amount of pressure has been applied to deliver the desired amount of liquid. The nib is preferably designed to deliver the liquid topically, such as a person's or animal's skin.

FIG. 1 is an illustration of a cross-sectional, exploded perspective view of one embodiment of the handheld topical applicator. As shown in FIG. 1, one embodiment of the handheld topical applicator 100 may comprise: a front cap 105, main housing 110, first nib 115, front housing 120, first reservoir 125, second reservoir 150, second cylinder 130, biasing member 135, first cylinder 140, plug 145, rear housing 155, second nib 160, and end cap 165. As discussed above, the housings (i.e., main housing 110, front housing 120, and rear housing 155) are preferably structures designed to house, fix, protect, guide, and/or engage with any of the inner components of the handheld topical applicator 100 by enabling the safe, correct, and comfortable handling of the handheld topical applicator 100 or any of its mechanisms. The main housing 110, front housing 105, and rear housing 155 may be constructed as a single piece or as multiple pieces and may also include other components (e.g., clip, additional nib(s)). The front cap 105 is preferably a cover that removeably attaches to the proximal end or front end of the handheld topical applicator 100 (i.e., main housing 110) and covers the first nib 115 to prevent unwanted contact between the first nib 115 and a surface. The front housing 120 is preferably the structure that comprises a chamber 123 that holds, contains, or houses the first reservoir 125, which stores liquid such as ink or topical medicine. The front housing 120 may comprise a first nib 115, which is preferably in contact or in fluid communication with the first reservoir 125, and the first nib 115 is preferably adapted to deliver a flow of liquid from the first reservoir 125 to a surface upon application of pressure to the first nib 115. The shank portion of the first nib 115 may extend towards the chamber 123 and the first reservoir 12 or may be separated by an intervening piece. The first nib 115 may also be constructed of any material such as porous polymer material (e.g., custom Porex® material), foam rubber, fiber, fiberglass, silicone rubber, fabric, or metal (e.g., gold, palladium silver, steel, brass, titanium). In one embodiment, the first nib 115 may be constructed of high-density polyethylene with a specific gravity of approximately 0.94 gm/cc. In other embodiments, the head portion of the first nib 115 may also contain a butadiene/styrene copolymer blended with the polyethylene. Importantly, the flow rate of the liquid traveling through the first nib 115 may also be dependent upon the porosity of the first nib 115 and the material density of the first reservoir 125. Furthermore, the first nib 115 may have various shapes to conform to a particular surface. For example, the face portion of the first nib 115 may be flat or may be curved. The surfaces, in which the first nib 115, may contact may be any external or outermost layer of an object, person, or environment, such that the handheld topical applicator 100 may be used for multiple applications, including medicinal applications.

The piston is preferably a structure that provides a counterforce to the first nib 115 after the first nib 115 is pushed inwards towards the main housing 110 and against the surface. The piston may comprise: a first cylinder 140, second cylinder 130, and biasing member 135 and one or more tabs (shown in FIG. 6). In another embodiment, a portion of the second cylinder 130 may be adapted to hold or secure the first reservoir 125. In other embodiments where the handheld topical applicator 100 may be reusable and not a single-use device, a user may also refill the first reservoir 125 by removing the first reservoir 125 from the front housing 120 and then refilling the first reservoir 125 with liquid. The biasing member 135 is preferably housed in-between the first cylinder 140 and second cylinder 130 and preferably provides biasing towards the distal end of the front housing 120. Specifically, the front housing 120 is preferably disposed inside the main housing 110, such that, a portion of the first nib 115 may protrude outside the central opening of the main housing 110. In one embodiment, the biasing member 135 may be a spring. A portion of the first nib 115 is preferably adapted to retract back into and through the central opening of the main housing upon compression of the first nib 115 onto a surface. In one embodiment, the first nib 115 may controllably retract within the opening of the main housing 110 due to the inner workings of the piston and tabs. The first nib 115 is also preferably adapted to project through the central opening of the main housing 110 due to the biasing of the piston (i.e., first cylinder 140, second cylinder 130, and biasing member 135) when pressure is not applied against the first nib 115. Although FIG. 1 shows a portion of the first cylinder 140 covering a portion the second cylinder 130, other embodiments of the handheld topical applicator 100 may have a portion of the second cylinder 130 covering a portion of the first cylinder 140.

FIG. 1 also shows that the front housing 120 may comprise a shoulder 118 and that the main housing 110 may comprise an inner flange 108. The shoulder 118 of the front housing 120 is generally designed to restrict the protrusion of the first nib 115 through the central opening of the main housing 110. Specifically, when the piston biases the front housing 120 towards the main housing 110, the shoulder 118 preferably contacts the inner flange 108 of the main housing 110, such that the protrusion of the first nib 115 through the central opening of the main housing 110 is restricted.

Additionally, the first nib 115 may be controllably retracted. As discussed above, the first nib 115 preferably protrudes at a precise distance due to contact between the shoulder 118 and inner flange 108. This, in-turn, preferably controls the pressure and audible/tactile feedback that ultimately determines the amount of liquid 125 being delivered by the handheld topical applicator 100.

Furthermore, FIG. 1 shows that the distal or rear portion of the handheld topical applicator 100 may comprise: a plug 145, rear housing 155, second nib 160, and end cap 165. Like the front housing 120, the rear housing 155 is also preferably a structure that contains a chamber 153 for holding and securing the second reservoir 150, which preferably stores liquid. The rear housing 155 may comprise a second nib 160, which is preferably in contact or in fluid communication with the second reservoir 150, and the second nib 160 preferably delivers a flow of liquid 150 from the second reservoir 153 to a surface upon application of pressure to the second nib 160 to the surface. The shank portion of the second nib 160 may extend towards the chamber 153 and second reservoir 150 or may be separated by an intervening piece. Additionally, the second nib 160 may be constructed of various materials such as porous polymer material (e.g., custom Porex® material), foam rubber, fiber, fiberglass, silicone rubber, fabric, or metal (e.g., gold, palladium silver, steel, brass, titanium). Like the first nib 115, one embodiment of the second nib 160 may be constructed of high-density polyethylene with a specific gravity of approximately 0.94 gm/cc. In other embodiments, the head portion of the second nib 160 may also contain a butadiene/styrene copolymer blended with the polyethylene Importantly, the flow rate of the liquid traveling through the second nib 160 may also be dependent upon the porosity of the second nib 160 and the material density of the second reservoir 150. Furthermore, the second nib 160 may comprise a pointed tip to provide the user with the ability to create thin strokes. The plug 145 is preferably an obstruction for blocking one end of the chamber 153 to prevent any leakage of the liquid from the second reservoir 150. The plug 145 may also be adapted to hold and/or secure a portion of the piston. The end cap 165 is preferably a cover that removeably attaches to the distal end of the handheld topical applicator 100 (i.e., rear housing 155) and may cover the second nib 160 to prevent unwanted contact of the second nib 160.

Finally, regarding the main housing 110, in one embodiment, the handheld topical applicator 100 may comprise a grip 170 for providing secured handling of the handheld topical applicator 100. In various embodiments, the grip 170 may be substantially curved with a plurality of dimples and/or may provide an aesthetic look.

In various embodiments, the handheld topical applicator 100 may be constructed as a single use or multi-use device. Specifically, for single-use applications, the fill volume of the liquid in the first reservoir 125 or second reservoir 150 may be the desired volume of liquid for delivery for a one-time, single-use application. Additionally, the flow rate of the liquid traveling through the nib may be dependent upon: (1) the porosity of the first nib 115 and/or second nib 160 and (2) the material density of the first reservoir 125 and/or second reservoir 150. Thus, in various embodiments, in order to achieve the single use application, the flow rates (i.e., porosity of nibs, material density of reservoirs) will preferably be calibrated accordingly, depending upon the type of application. In various embodiments, a single-use handheld topical applicator maybe used in a single application, but for multiple areas, allowing the full dose to be delivered potentially in more than one location. Conversely, in various embodiments for a multi-use device, the reservoir and reservoir chamber size might be larger in order to hold and store a larger amount of liquid.

Figure 2:
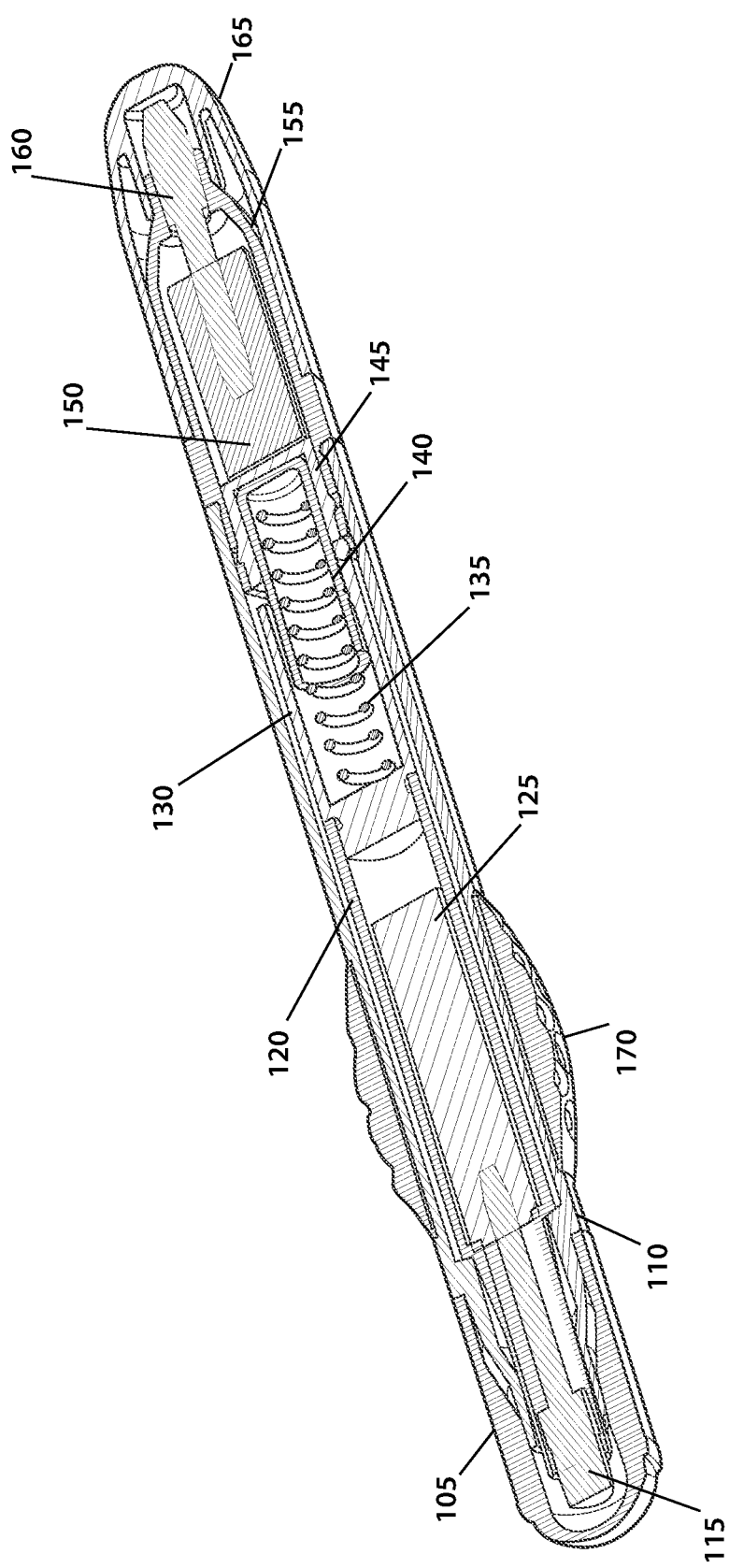
FIG. 2 is an illustration of a cross-sectional, assembled perspective view of one embodiment of the handheld topical applicator.

FIG. 2 is an illustration of a cross-sectional, assembled perspective view of one embodiment of the handheld topical applicator. As shown in FIG. 2, one embodiment of the handheld topical applicator 100 may comprise: a front cap 105, main housing 110, first nib 115, front housing 120, first reservoir 125, second reservoir 150, second cylinder 130, biasing member 135, first cylinder 140, plug 145, rear housing 155, second nib 160, and end cap 165. FIG. 2 shows that first reservoir 125 may be stored in the chamber 123 of the front housing 120. Additionally, the first nib 115 is preferably coupled to the proximal end of the front housing 120, and the shank portion of the first nib 115 may be in contact with liquid stored in the reservoir 125, such that the liquid may flow through proximal end of the first nib 115. The piston, which may comprise a first cylinder 140, second cylinder 130, and biasing member 135, is preferably positioned behind the distal end of the front housing 120 and may be adapted to provide a biasing mechanism for the front housing 120. The main housing 110 is preferably adapted to house or enclose the front housing 120, its components (e.g., first nib 115, first reservoir 125) and may comprises a front cap 105, which is removeably connected to the forward end of the main housing 110. The main housing 110 may also comprises a grip 170.

Regarding the rear portion of the handheld topical applicator 100 (i.e., plug 145, second reservoir 150, rear housing 155, second nib 160, and end cap 165), the rear portion of the handheld topical applicator 100 may be designed to provide the user with the ability for creating thin strokes. The plug 145 is preferably coupled to the front end or proximal end of the rear housing 155 and preferably adapted to seal the second reservoir 150 housed in the rear housing 155. The second nib 160 is preferably coupled to the distal end of the rear housing 155, and preferably, the end cap 165 may be removeably coupled to the distal end of the rear housing 155.

Figure 3:
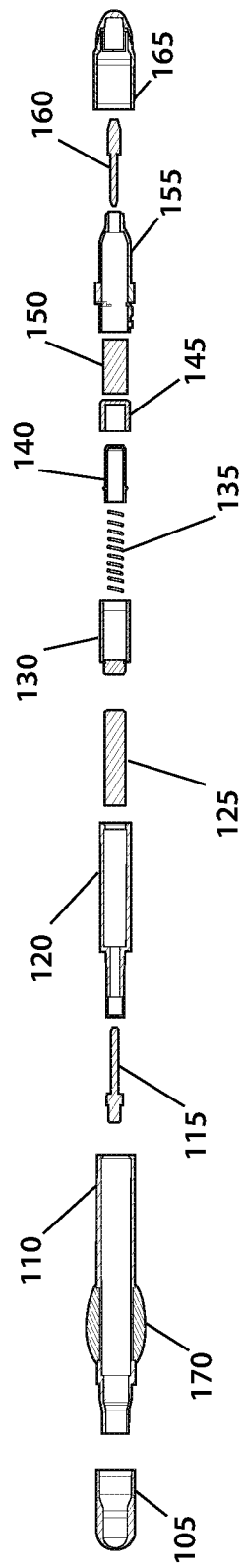
FIG. 3 is an illustration of a cross-sectional, exploded top view of one embodiment of the handheld topical applicator.

FIG. 3 is an illustration of a cross-sectional, exploded top view of one embodiment of the handheld topical applicator. As shown in FIG. 3, one embodiment of the handheld topical applicator 100 may comprise: a front cap 105, main housing 110, first nib 115, front housing 120, first reservoir 125, second reservoir 150, second cylinder 130, biasing member 135, second cylinder 140, plug 145, rear housing 155, second nib 160, and end cap 165.

Figure 4:
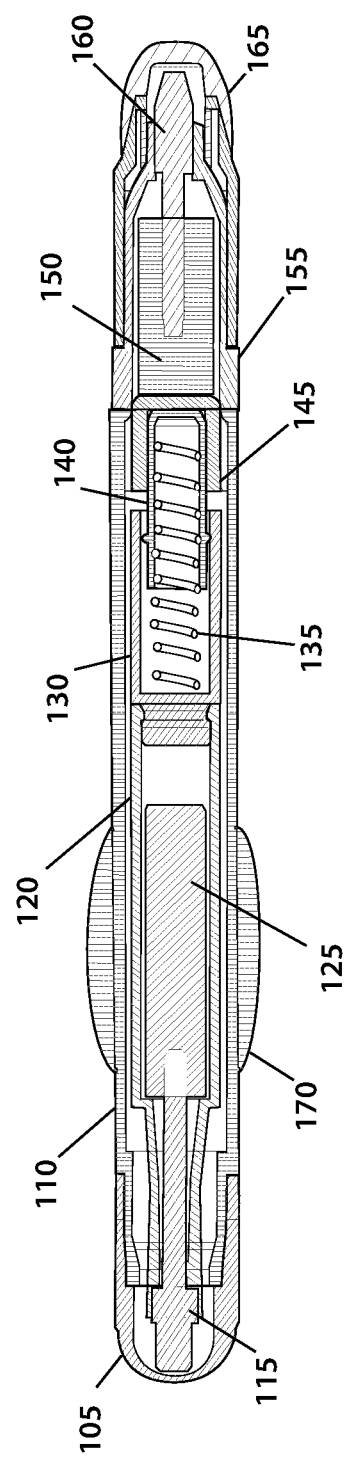
FIG. 4 is an illustration of a cross-sectional, assembled top view of one embodiment of the handheld topical applicator.

FIG. 4 is an illustration of a cross-sectional, assembled top view of one embodiment of the handheld topical applicator. As shown in FIG. 4, one embodiment of the handheld topical applicator 100 may comprise: a front cap 105, main housing 110, first nib 115, front housing 120, first reservoir 125, second reservoir 150, second cylinder 130, biasing member 135, first cylinder 140, plug 145, rear housing 155, second nib 160, and end cap 165.

Figure 5:
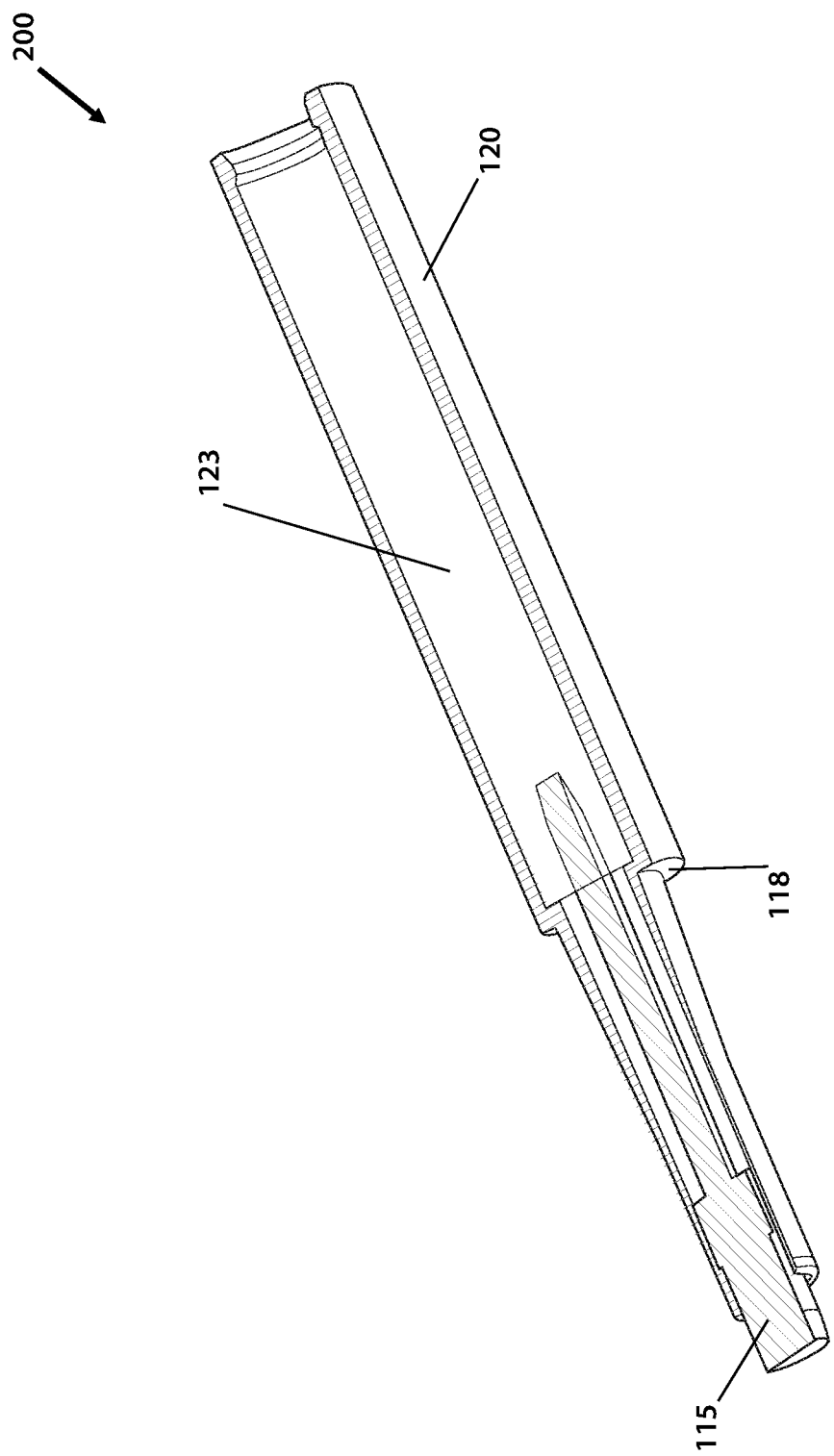
FIG. 5 is an illustration of a cross-sectional, perspective view of one embodiment of the front housing assembly.

FIG. 5 is an illustration of a cross-sectional, perspective view of one embodiment of the front housing assembly. As shown in FIG. 5, one embodiment of the front housing assembly 200 may comprise: a front housing 120 and first nib 115. The front housing 120 may also comprise a chamber 123 and shoulder 118. Preferably the first reservoir 125 is stored in the chamber 123 of the front housing 120 and preferably the first nib 115 is coupled to the proximal end or front portion of the front housing 120. The shank portion or rear end of the first nib 115 preferably extends towards the chamber 123 of the front housing 120, such that the first nib 115 may contact the liquid stored in the first reservoir 125.

Figure 6:
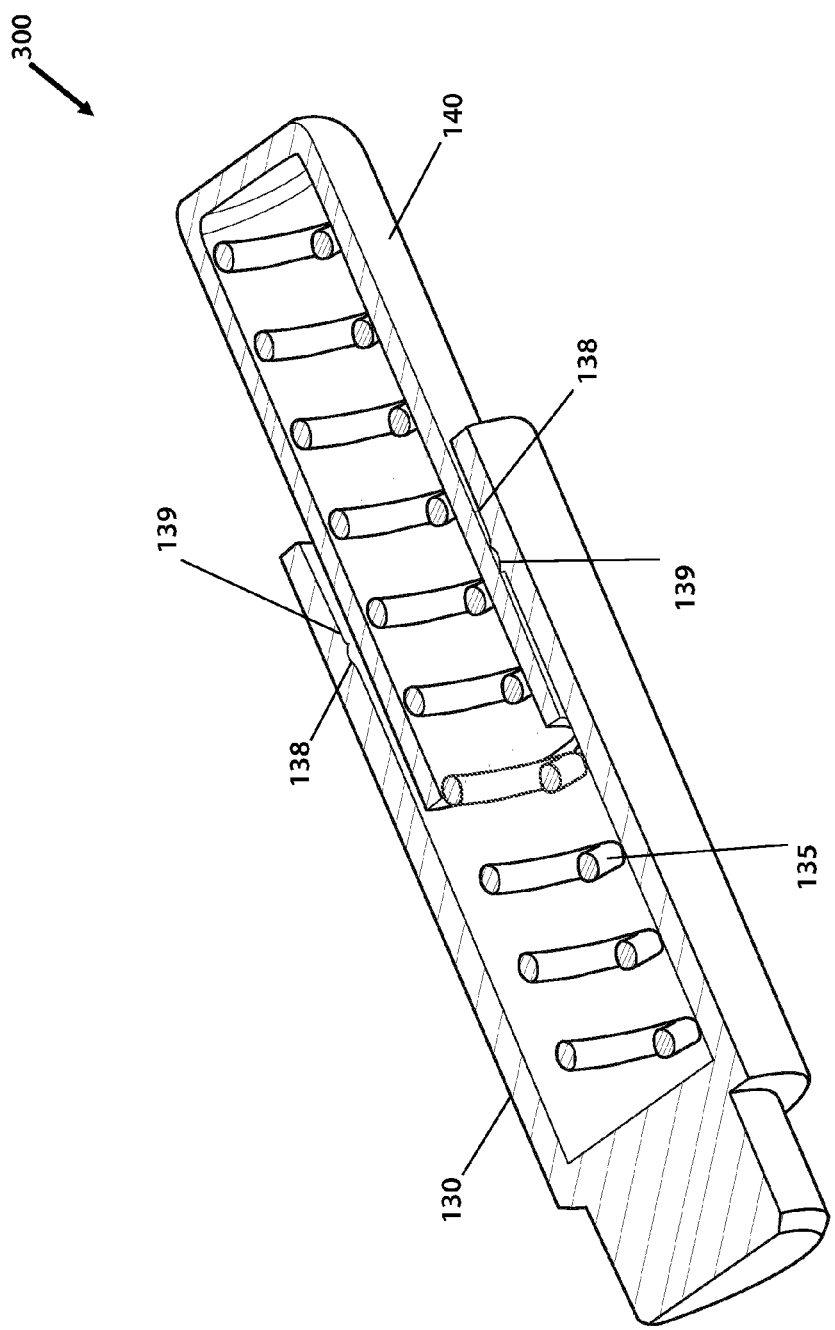
FIG. 6 is an illustration of a cross-sectional, perspective view of one embodiment of the piston.

FIG. 6 is an illustration of a cross-sectional, perspective view of one embodiment of the piston. As shown in FIG. 6, one embodiment of the piston 300 may comprise: a first cylinder 140, second cylinder 130, biasing member 135, first tabs 138, and second tabs 139. The biasing member 135 is preferably disposed in-between and within the first cylinder 140 and second cylinder 130 and preferably provides a biasing mechanism for the piston 300. In one embodiment, the biasing member 135 may be a spring. The first tabs 138 are preferably positioned on the outer surface or exterior of the first cylinder 140, and the second tabs 139 are preferably positioned on the inner surface or interior of the second cylinder 130. The first tabs 138 and second tabs 139 are preferably adapted to contact each other when first nib 115 and front housing 120 press against the piston 300 (i.e., the second cylinder 130 compressing the biasing member 135 against the first cylinder 140) and preferably create an audible sound upon contact with each other. Thus, an audible click may be heard when the biasing member 135 is compressed. Specifically, the first tabs 138 and second tabs 139 may create an audible click due to any interfering plastic that rides against the biasing member 135. Contact between the first tabs 138 and second tabs 139 may also preferably create a tactile response when the user presses the first nib 115 against a surface. In various embodiments, the tactile response may be a physical feedback or haptic feedback such as a force, vibration, motion, and/or click. Preferably, the biasing member 135, location of the first tabs 138 and second tabs 139, nib materials, and reservoir materials, in combination, help control the desired flow rate to achieve a passive time release of the liquid. This passive time release preferably creates a delivery of a desired amount of liquid when the user hears an audible "click" and/or feels a tactile response originating from contact of the first tabs 138 and second tabs 139.

Figure 7:
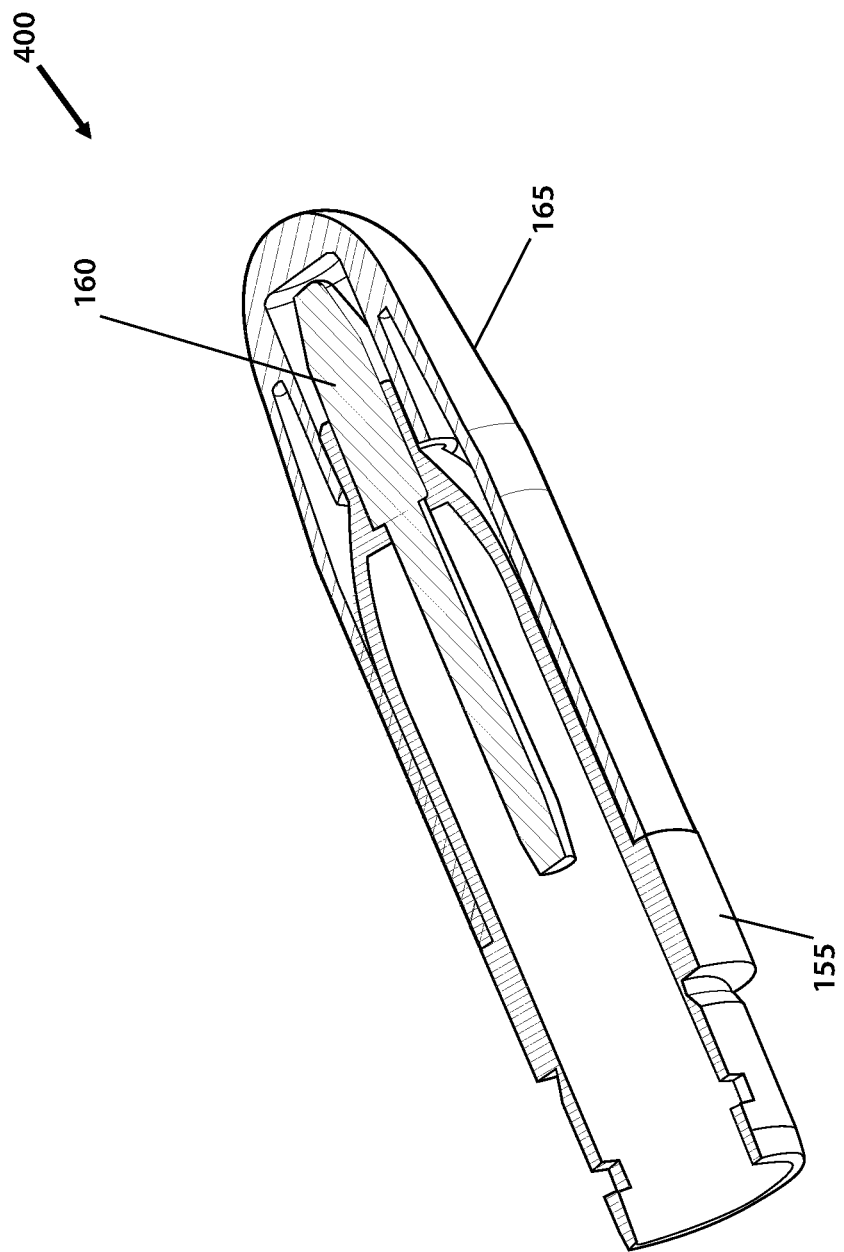
FIG. 7 is an illustration of a cross-sectional, perspective view of one embodiment of the rear housing assembly.

FIG. 7 is an illustration of a cross-sectional, perspective view of one embodiment of the rear housing assembly. As shown in FIG. 7, one embodiment of the rear housing assembly 400 may comprise: a rear housing 155, second nib 160, and end cap 165. FIG. 7 shows that the second nib 160 is preferably coupled to the distal end of the rear housing 155. Additionally, the end cap 165 may be coupled to the distal end of the rear housing 155 and preferably removeably covers the rear end of the second nib 160.

Figure 8:
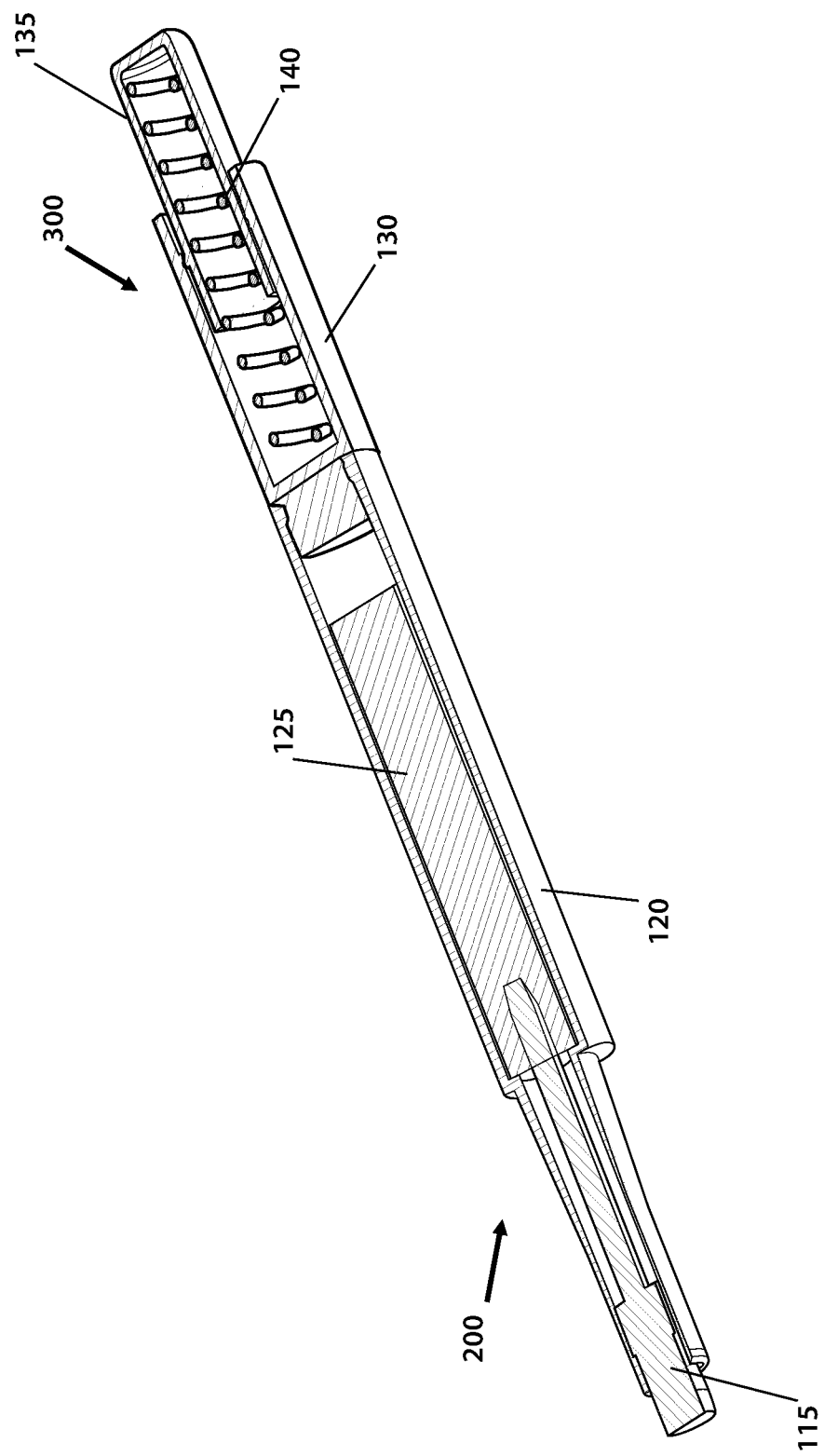
FIG. 8 is an illustration of a cross-sectional, perspective view of one embodiment of the front housing assembly and shows how the reservoir of the front housing assembly is filled with liquid.

FIG. 8 is an illustration of a cross-sectional, perspective view of one embodiment of the front housing assembly and shows how the reservoir of the front housing assembly is filled with liquid. As shown in FIG. 8, both the front housing assembly 200 and the piston 300 may comprise: a first nib 115, front housing 120, first reservoir 125, second cylinder 130, first cylinder 140, and biasing member 135. The first nib 115 is preferably coupled to the proximal end or front end portion of the front housing 120. A portion of the second cylinder 130 of the piston 300 may removeably coupled to the rear portion or distal end of the front housing 120, such that the second cylinder 130 may function as a plug to seal the chamber 123 within the front housing 120. A liquid stored in the first reservoir 125 of the front housing 120 may travel through the first nib 115 when pressure by a surface is applied against the first nib 115. The biasing member 135 preferably provides the biasing or counter force to project the front housing assembly 120 through the main housing 110.

Figure 9:
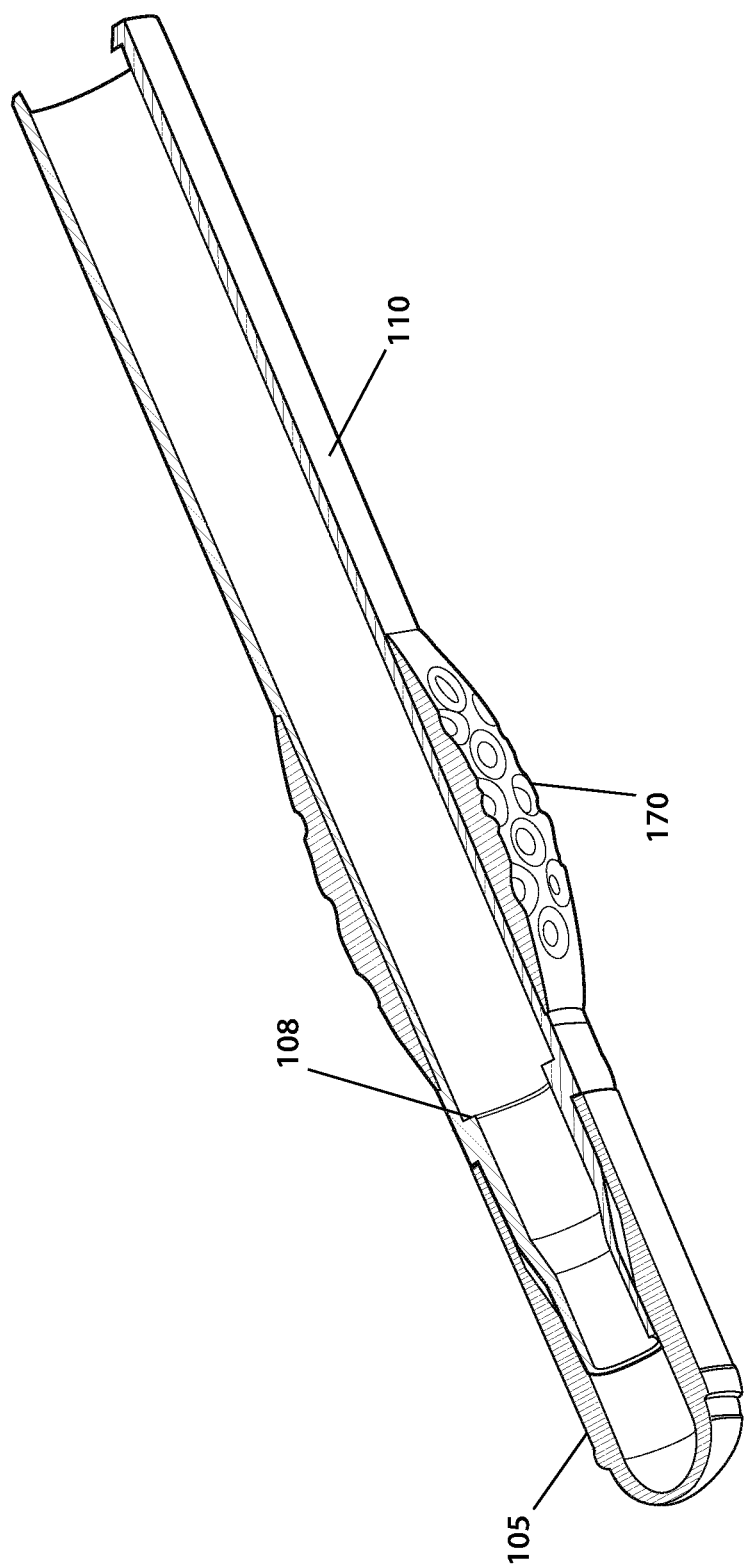
FIG. 9 is an illustration of a cross-sectional, perspective view of one embodiment of the main housing and front cap and shows how the front cap may be coupled to the main housing.

FIG. 9 is an illustration of a cross-sectional, perspective view of one embodiment of the main housing and front cap and shows how the front cap may be coupled to the main housing. As shown in FIG. 9, the main housing 110 may comprise: a grip 170 and an inner flange 108. FIG. 9 shows that the front cap 105 may removeably attach to the proximal end or front portion of the main housing 110.

Figure 10:
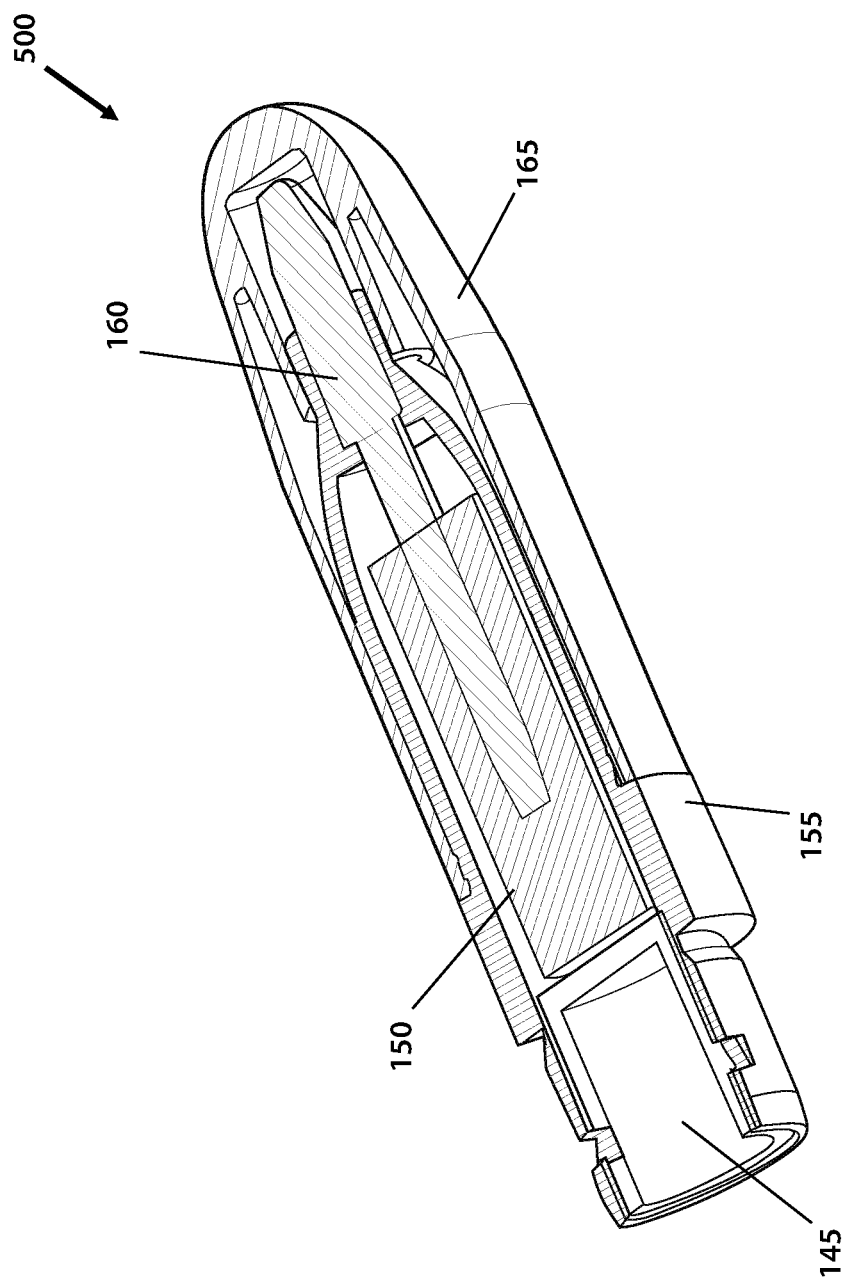
FIG. 10 is an illustration of a cross-sectional, perspective view of one embodiment of the rear housing assembly and shows how the reservoir of the rear housing assembly is filled with liquid.

FIG. 10 is an illustration of a cross-sectional, perspective view of one embodiment of the rear housing assembly and shows how the reservoir of the rear housing assembly is filled with liquid. As shown in FIG. 10, one embodiment of the rear housing assembly 500 may comprise: a plug 145, liquid 150, rear housing 155, second nib 160, and end cap 165. Preferably, the plug 145 is removeably coupled to the proximal end or front end portion of the rear housing 155. The second nib 160 is preferably coupled to the rear end portion or distal end of the rear housing 155. Liquid is typically stored within the second reservoir 150, and the second reservoir 150 may be filled with liquid when the second reservoir 150 is removed from the rear housing 155. This may be accomplished when the plug 145 is removed. The end cap 165 may be removeably coupled to the rear end portion or distal end of the rear housing assembly 500.

Figure 11:
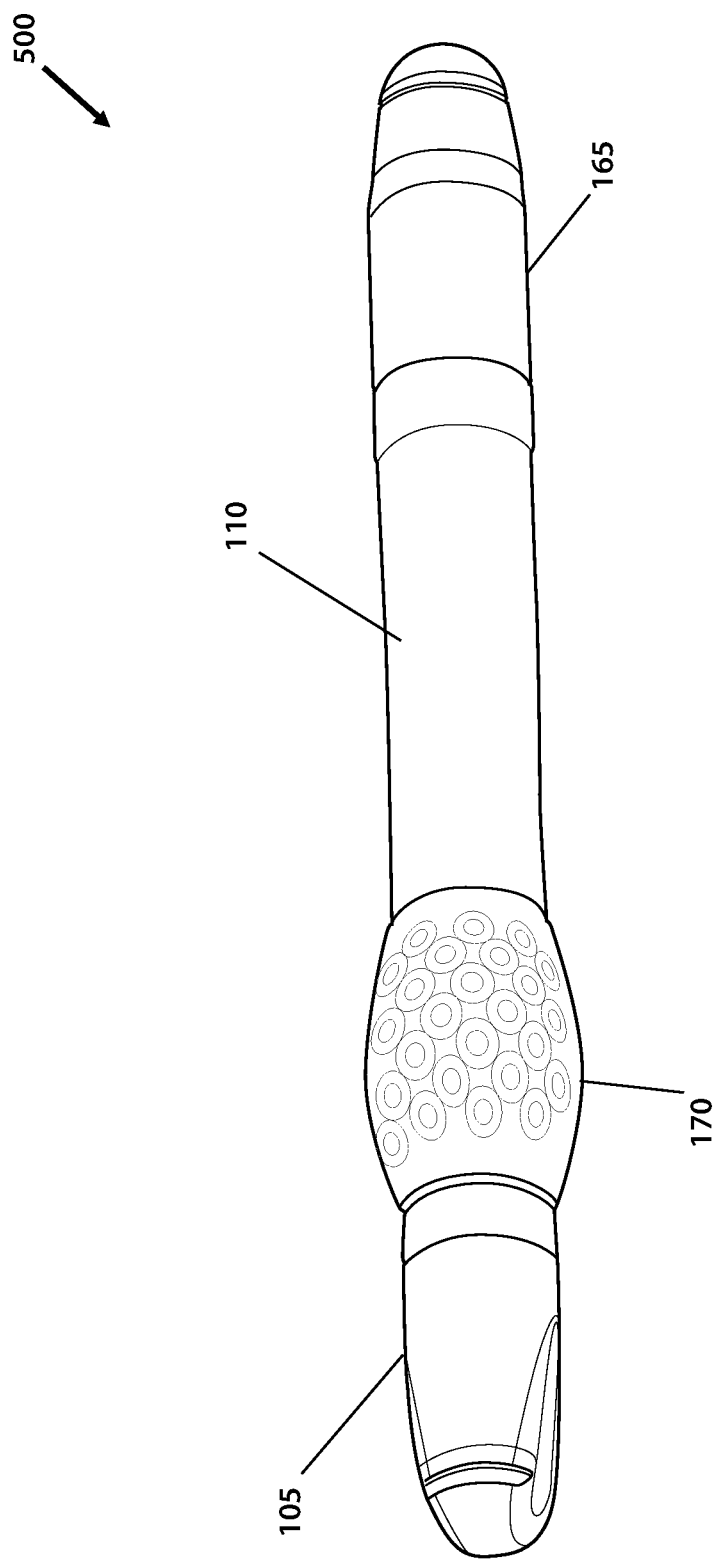
FIG. 11 is an illustration of a perspective view of one embodiment of the handheld topical applicator.

FIG. 11 is an illustration of a perspective view of one embodiment of the handheld topical applicator. As shown in FIG. 11, one embodiment of the handheld topical applicator 600 may comprise: a front cap 105, main housing 110, rear housing 155, and end cap 165. Preferably, the front cap 105 is removeably coupled to the proximal end or front end portion of the main housing 110. Preferably, the rear housing 155 is removeably coupled to the rear end portion of the main housing 110. The end cap 165 may be removeably coupled to the distal end or rear portion of the rear housing 110.

FIG. 11 also shows that the main housing 110 may comprise a grip 170. The grip 170 may be shaped with aesthetic features. For example, in one embodiment, the grip 170 may contain a plurality of dimples, such that the grip 170 may resemble the surface of a golf ball.

Figure 12:
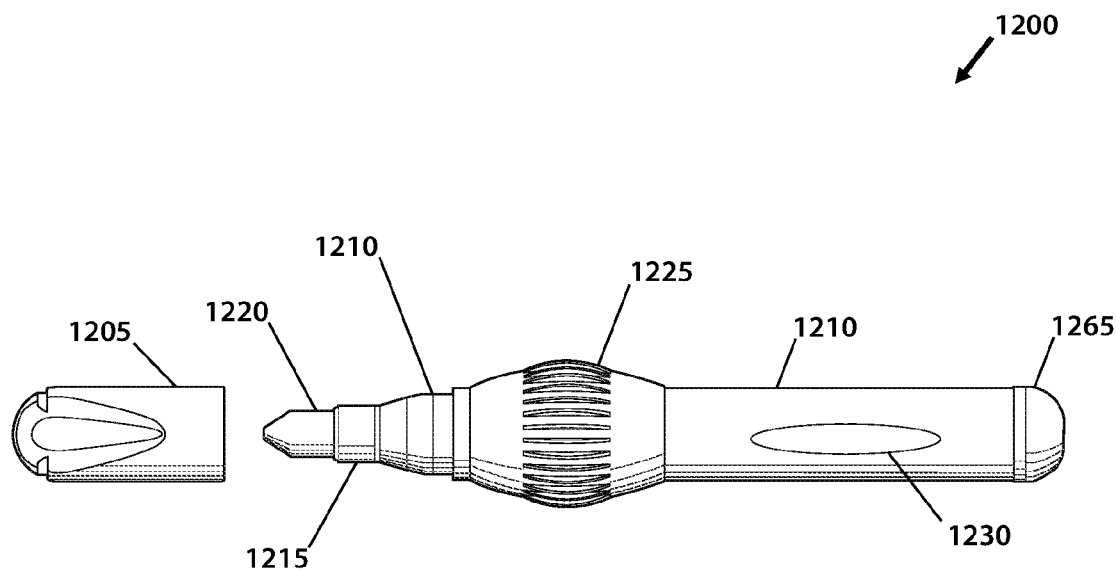
FIG. 12 is an illustration of another embodiment of the handheld topical applicator.

FIG. 12 is an illustration of another embodiment of the handheld topical applicator. As shown in FIG. 12, another embodiment of the handheld topical applicator 1200 may include a single nib design. Specifically, another embodiment of the handheld topical applicator 1200 may comprise: a front cap 1205, main housing 1210, front housing 1215, nib 1220 (e.g., first nib), grip 1225, a window indicator 1230, and end cap 1265. Preferably, the front cap 1205 is adapted to removeably couple to the proximal end or front end portion of the main housing 1210. Similarly, the end cap 1265 is preferably adapted to removeably couple to the distal end or rear portion of the main housing 1210.

Importantly, FIG. 12 shows that the handheld topical applicator 1200 may comprise a window indicator 1230. The window indicator 1230 may reveal the reservoir of the handheld topical applicator 1200 to show the remaining amount of liquid left in the handheld topical applicator 1200. In various embodiments, the front housing 1215 may be constructed with transparent material to allow a user to view the reservoir stored in the chamber of the front housing 1215. FIG. 12 also shows that the main housing 1210 may also comprise a grip 1225 to provide better contour and ergonomics. The grip 1225 may be shaped with aesthetic features.

Figure 13:
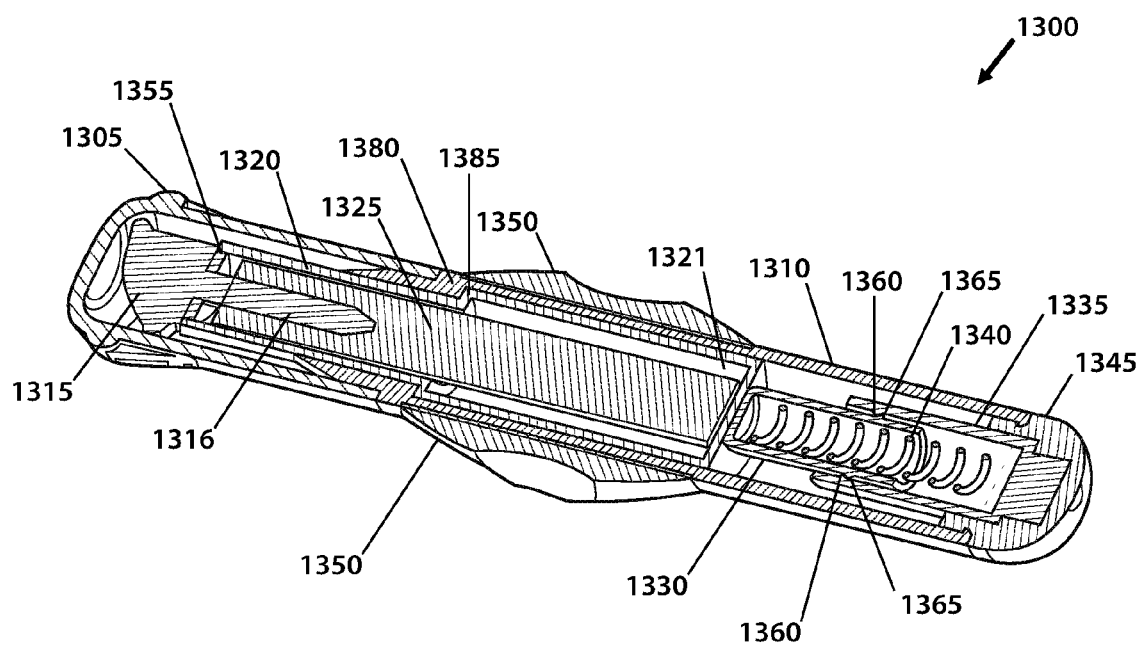
FIG. 13 is an illustration of a cross-sectional, assembled perspective view of another embodiment of the handheld topical applicator.

FIG. 13 is an illustration of a cross-sectional, assembled perspective view of another embodiment of the handheld topical applicator. As shown in FIG. 13, another embodiment of the handheld topical applicator 1300 may comprise: a front cap 1305, main housing 1310, nib 1315 (e.g., first nib), front housing 1320, reservoir 1325, first cylinder 1330, second cylinder 1335, biasing member 1340, end cap 1345, grip 1350, and collar 1355. The main housing 1310 and front housing 1320 are preferably designed to house and secure the inner components of the handheld topical applicator 100 and may be constructed as a single piece or multiple pieces. The front cap 1305 may be adapted to removeably attach to the proximal end or front end portion of the handheld topical applicator 1300 and preferably covers the nib 1315 to prevent unwanted contact of the nib 1315. The front housing 1320 preferably comprises a chamber 1321 that holds and contains a reservoir 1325 for storing liquid. The nib 1315 may be coupled to the proximal end of the front housing 1320 and the shank portion 1316 of the nib 1315 is preferably in contact or in fluid communication with the reservoir 1325. In other embodiments, the nib 1315 may also be coupled to the front housing 1320 via a collar 1355, which is preferably adapted to hold and secure the nib 1315 to the front housing 1320. The shank portion 1316 of the nib 1315 may extend towards the chamber 1321 and reservoir 1325. The nib 1315 may be constructed of any material such as porous polymer material (e.g., custom Porex® material), foam rubber, fiber, fiberglass, silicone rubber, fabric, or metal (e.g., gold, palladium silver, steel, brass, titanium). For example, in one embodiment, the nib 1315 may be constructed of high-density polyethylene with a specific gravity of 0.94 gm/cc. The head portion of the nib 1315 may also be constructed with a butadiene/styrene copolymer blended with polyethylene Importantly, the nib 1315 may have various shapes to conform to a particular surface, such that the handheld topical applicator 1300 may be used for multiple applications. In various embodiments, the handheld topical applicator 1300 may be constructed with a nib 1315 that may be replaceable with other nibs of various sizes and shapes.

Importantly, the flow rate of the liquid traveling through the nib 1315 may also be dependent upon the porosity of the nib 1315 and the material density of the reservoir 1325. The nib 1315 may also have various shapes to conform to a particular surface, such that the handheld topical applicator 1300 may be used for various applications.

The piston preferably provides a counterforce to the front housing 1320 and nib 1315 after the nib 1315 and front housing 1320 are pushed inwards towards the piston and against the surface. The piston may comprise: a first cylinder 1330, second cylinder 1335, biasing member 1340, first tabs 1360, and second tabs 1365. The biasing member 1340 is preferably housed in-between the first cylinder 1330 and second cylinder 1335 and preferably provides biasing towards the distal end of the front housing 1320. In one embodiment, the biasing member 1340 may be a spring. Like the previous embodiments, the front housing 1320 is preferably positioned within the main housing 1310, such that, a portion of the front housing 1320 or nib 1315 may protrude outside the central opening of the main housing 1310. Thus, the front housing 1320 and nib 1315 are preferably adapted to retract back into and through the central opening of the main housing 1310 once pressure is applied to the nib 1315. The nib 1315 and front housing 1320 are also preferably adapted to project through the central opening of the main housing 1310 due to the biasing of the piston (i.e., first cylinder 1330, second cylinder 1335, and biasing member 1340) when pressure is not applied against the nib 1315. Preferably, the biasing member 1340, location of the first tabs 1360 and second tabs 1365, nib materials, and reservoir materials, in combination, help control the desired flow rate to achieve a passive time release of the liquid. This passive time release preferably creates a delivery of a desired amount of liquid when the user hears an audible "click" and/or feels a tactile response originating from contact of the first tabs 1360 and second tabs 1365. Although FIG. 13 shows a portion of the second cylinder 1335 covering a portion the first cylinder 1330, other embodiments of the handheld topical applicator 1300 may have a portion of the first cylinder 1330 covering a portion of the second cylinder 1335.

FIG. 13 also shows that the front housing 1320 may comprise a shoulder 1385 and that the main housing 1310 may comprise an inner flange 1380. The shoulder 1385 of the front housing 1320 is generally designed to restrict the protrusion of the front housing 1320 through the central opening of the main housing 1310. Specifically, when the piston biases the front housing 1320 towards the main housing 1310, the shoulder 1385 preferably contacts the inner flange 1380 of the main housing 1310, such that the protrusion of the front housing 1320 and nib 1315 through the central opening of the main housing 1310 is restricted.

Additionally, the retraction of the nib 1315 and front housing 1320 is preferably controlled. The nib 1315 preferably protrudes at a precise distance due to contact between the shoulder 1385 and inner flange 1380. This, in-turn, preferably controls the pressure and audible/tactile feedback that ultimately determines the amount of liquid being delivered by the handheld topical applicator 1300.

As shown in FIG. 13, the handheld topical applicator 1300 may comprise a grip 1350 for providing secured handling of the handheld topical applicator 1300. The grip 1350 may also be substantially curved and may provide an aesthetic look.

Figure 14:
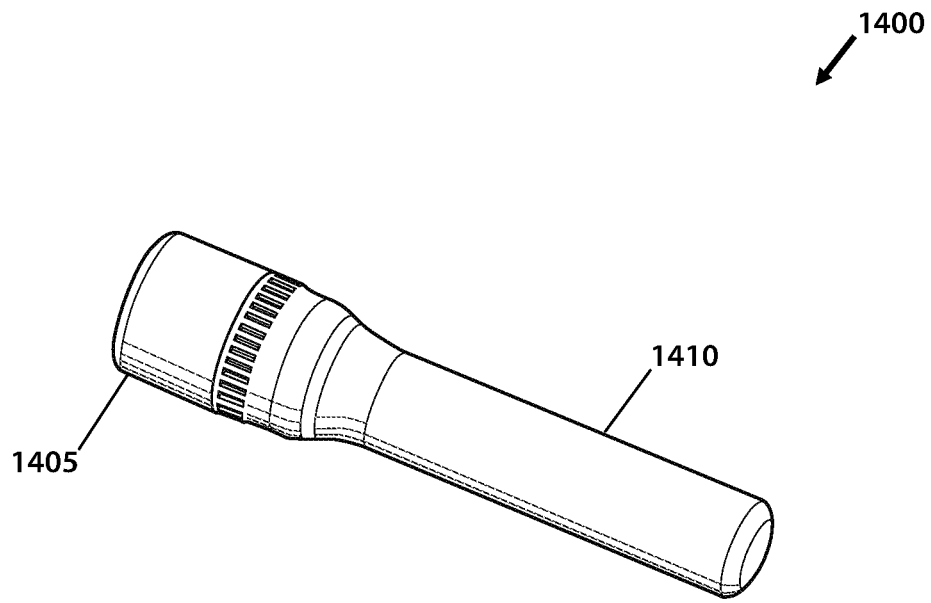
FIG. 14 is an illustration of another embodiment of the handheld topical applicator.

FIG. 14 is an illustration of another embodiment of the handheld topical applicator. Like the embodiments shown in FIGS. 12 and 13, one embodiment of the handheld topical applicator 1400 may include a single nib design. Specifically, another embodiment of the handheld topical applicator 1400 may comprise: a front cap 1405 and main housing 1410. Importantly, FIG. 14 shows that an embodiment of the handheld topical applicator 1400 may also lack a grip and/or end cap.

Figure 15:
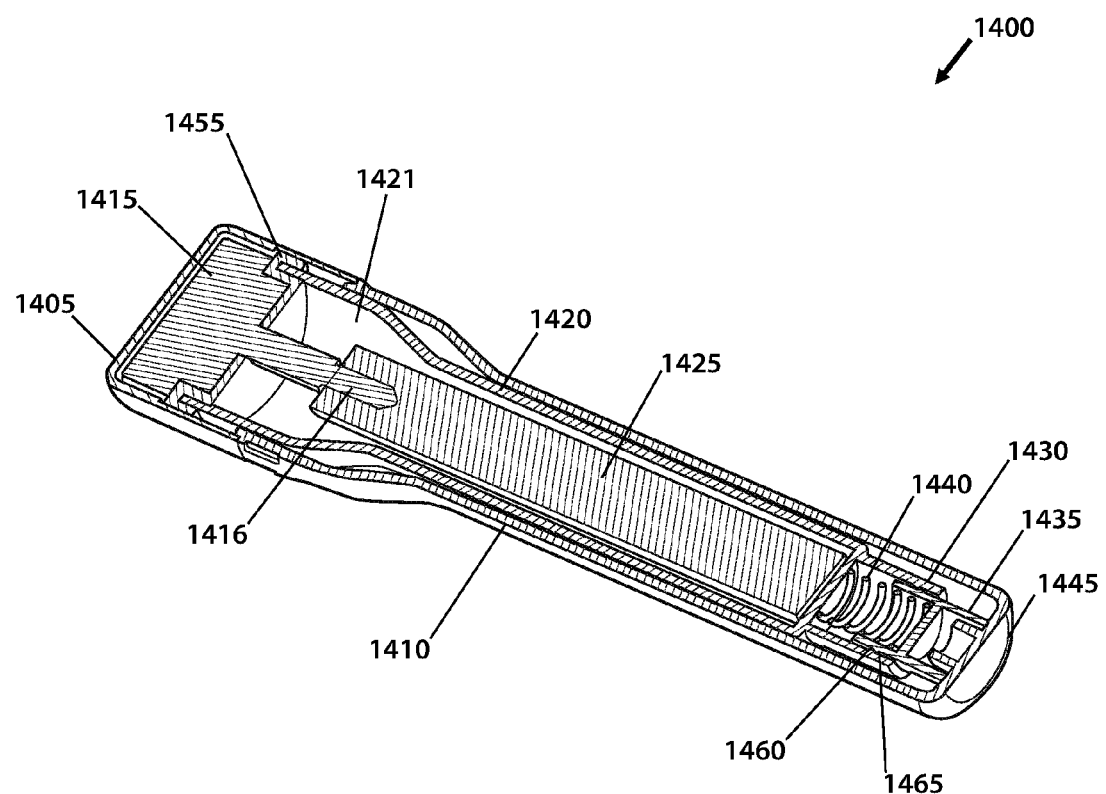
FIG. 15 is an illustration of a cross-sectional, assembled perspective view of another embodiment of the handheld topical applicator.

FIG. 15 is an illustration of a cross-sectional, assembled perspective view of another embodiment of the handheld topical applicator. As shown in FIG. 15, another embodiment of the handheld topical applicator 1400 may utilize a single nib design and may comprise: a front cap 1405, main housing 1410, nib 1415, front housing 1420, reservoir 1425, first cylinder 1430, second cylinder 1435, biasing member 1440, end cap 1445, collar 1455, first tabs 1460, and second tabs 1465. FIG. 15 shows that the front housing 1420 may comprise a chamber 1421 that holds and secures the reservoir 1425 for storing liquid. The nib 1415 may be coupled to the proximal end of the front housing 1420, and the shank portion 1416 of the nib 1415 is preferably in contact or in fluid communication with the reservoir 1425. This embodiment of the handheld topical applicator 1400 also shows that the nib 1415 coupled to the front housing 1420 via a collar 1455, which is preferably adapted to hold and secure the nib 1415 to the front housing 1420. The shank portion 1416 of the nib 1415 may extend towards the chamber 1421 and reservoir 1425. The nib 1415 may be constructed of any material such as porous polymer material (e.g., custom Porex® material), foam rubber, fiber, fiberglass, silicone rubber, fabric, or metal (e.g., gold, palladium silver, steel, brass, titanium). For example, in one embodiment, the nib 1415 may be constructed of high-density polyethylene with a specific gravity of 0.94 gm/cc. The head portion of the nib 1415 may also be constructed with a butadiene/styrene copolymer blended with polyethylene. Importantly, the nib 1415 may have various shapes to conform to a particular surface, such that the handheld topical applicator 1400 may be used for multiple applications. In various embodiments, the handheld topical applicator 1400 may be constructed with a nib 1415 that may be replaceable with other nibs of various sizes and shapes. The flow rate of the liquid traveling through the nib 1415 may also be dependent upon the porosity of the nib 1415 and the material density of the reservoir 1425. Preferably, the biasing member 1440, location of the first tabs 1460 and second tabs 1465, nib materials, and reservoir materials, in combination, help control the desired flow rate to achieve a passive time release of the liquid. This passive time release preferably creates a delivery of a desired amount of liquid when the user hears an audible "click" and/or feels a tactile response originating from contact of the first tabs 1460 and second tabs 1465.

In various embodiments, the handheld topical applicator 1200, 1300, 1400 may be constructed as a single use or multi-use device. Specifically, for single-use applications, the fill volume of the liquid in the reservoir 1325, 1425 may be the desired volume of liquid for delivery for a one-time, single-use application. Additionally, the flow rate of the liquid traveling through the nib 1315, 1415 may be dependent upon: (1) the porosity of the nib 1315, 1415 and (2) the material density of the reservoir 1325, 1425. Thus, in various embodiments, in order to achieve the single use application, the flow rates (i.e., porosity of nibs, material density of reservoirs) will preferably be calibrated accordingly, depending upon the type of application or use. In various embodiments, a single-use handheld topical applicator maybe used in a single application, but for multiple areas, allowing the full dose to be delivered potentially in more than one location. Conversely, in other embodiments involving a multi-use device, the reservoir 1325, 1425 and reservoir chamber size might be larger in order to hold and store a larger amount of liquid.

Finally, although FIG. 15 shows a portion of the first cylinder 1430 covering a portion the second cylinder 1435, other embodiments of the handheld topical applicator 1400 may have a portion of the second cylinder 1435 covering a portion of the first cylinder 1430.

Figure 16A:
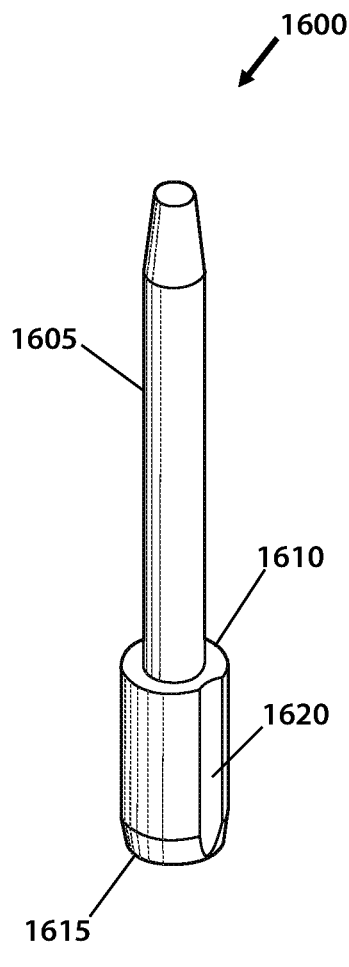
FIGS. 16A and 16B are illustrations of another embodiment of the nib.
Figure 16B:
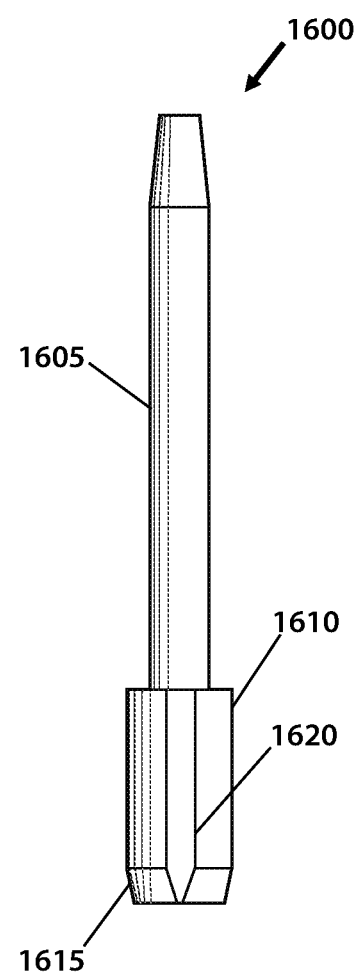

FIGS. 16A and 16B are illustrations of another embodiment of the nib. As shown in FIGS. 16A and 16B, another embodiment of the nib 1600 may comprise: a shank portion 1605, head portion 1610, and face portion 1615. The nib 1600 is preferably adapted to couple to the proximal end of a front housing or distal end of a rear housing. The shank portion 1605 is also preferably adapted to contact or otherwise engage with a liquid in a reservoir such that liquid stored inside the reservoir may be transferred from the shank portion 1605 to the head portion 1610 of the nib 1600. Preferably, the face portion 1615 of the nib is adapted to contact a surface, such as the skin of a recipient. Preferably, the porosity of the nib 1600 is calibrated based upon the desired flow rate for a specific type of application. In various embodiments, the nib 1600 may be constructed with anti-microbial material.

FIGS. 16A and 16B also show that an embodiment of the nib 1600 may comprise a notch 1620, which may be used to help engage, secure, and retain the nib 1600 onto the front housing or rear housing. FIGS. 16A and 16B also show that the face portion 1615 of the nib 1600 may be substantially flat and planar. Additionally, FIGS. 16A and 16B show that the shank portion 1605 may be substantially longer and/or thinner than the head portion 1610 of the nib 1600.

FIG. 17A and 17B are illustrations of another embodiment of the nib. As shown in FIGS. 17A and 17B, another embodiment of the nib 1700 may comprise: a shank portion 1705, head portion 1710, and face portion 1715. As shown in previous figures, the nib may be adapted to couple to the proximal end of a front housing or distal end of a rear housing. Additionally, the shank portion 1705 is preferably in contact with a liquid in a reservoir, such that liquid may transfer from the shank portion 1705 to the head portion 1710 of the nib 1700. The face portion 1715 of the nib is preferably used to contact a surface in order to impart a desired amount of the liquid in the reservoir. Preferably, the porosity of the nib 1700 is calibrated based upon the desired flow rate for a specific type of application. In various embodiments, the nib 1700 may be constructed with anti-microbial material.

FIGS. 17A and 17B also show that another embodiment of the nib 1700 may comprise a relatively shorter shank portion 1705. This may allow a quicker transfer liquid from the reservoir to the head portion 1710 and face portion 1715 of the nib 1700. Finally, FIGS. 17A and 17B show that the face portion 1715 of the nib 1700 may be slightly curved, angled, and not flat.

Figure 18A:
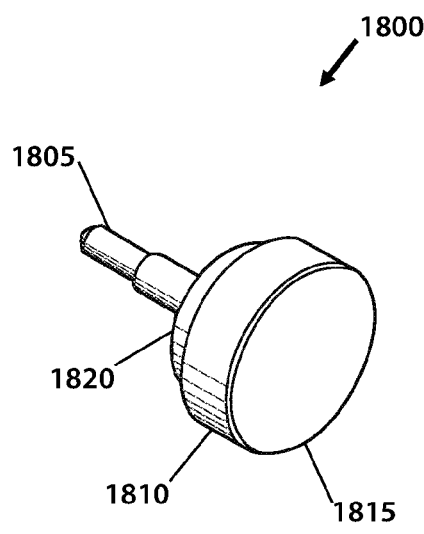
FIGS. 18A and 18B are illustrations of another embodiment of the nib.
Figure 18B:
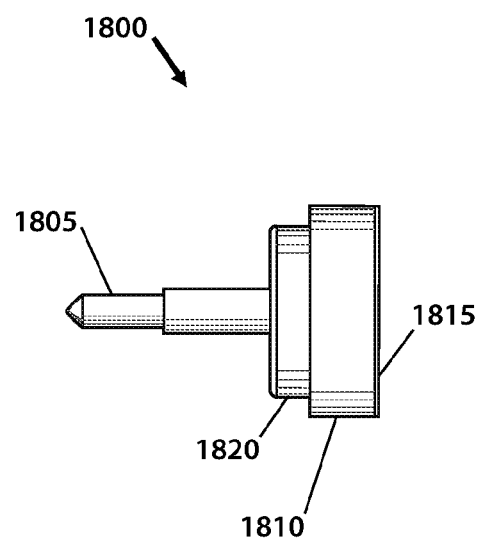

FIGS. 18A and 18B are illustrations of another embodiment of the nib. As shown in FIGS. 18A and 18B, another embodiment of the nib 1800 may comprise: a shank portion 1805, head portion 1810, face portion 1815, and collar portion 1820. The shank portion 1805 is preferably adapted to contact a reservoir, so that liquid may transfer from the shank portion 1805 to the head portion 1810 of the nib 1800. The face portion 1815 of the nib is preferably used to contact a surface. Preferably, the porosity of the nib 1800 is calibrated based upon the desired flow rate for a specific type of application. In various embodiments, the nib 1600 may be constructed with anti-microbial material.

Importantly, FIGS. 18A and 18B also show that an embodiment of the nib 1800 may comprise a collar portion 1820. The collar portion 1820 is used to help engage and secure the nib 1800 onto a housing by having the collar portion 1820 engage with a collar of a handheld topical applicator. In other embodiments, the collar portion 1820 may engage directly with the front housing or rear housing of the handheld topical applicator. FIGS. 18A and 18B also show that the nib 1800 may have a shorter shank portion 1805 and a flat face portion 1815.

Figure 19A:
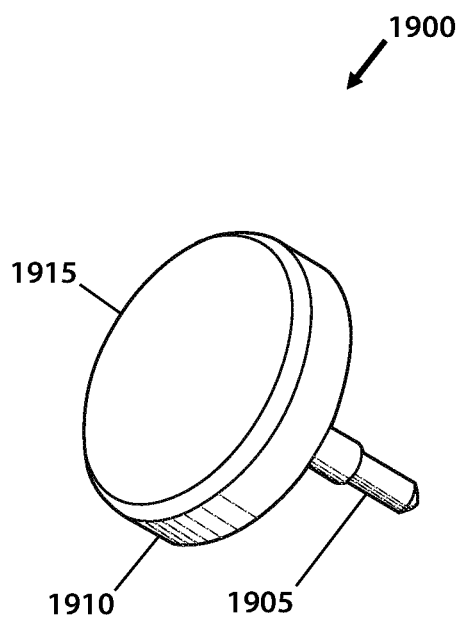
FIGS. 19A and 19B are illustrations of another embodiment of the nib.
Figure 19B:
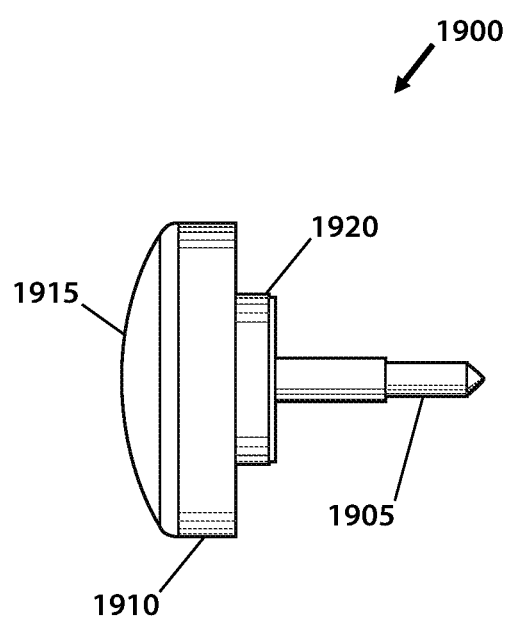

FIGS. 19A and 19B are illustrations of another embodiment of the nib. As shown in FIGS. 19A and 19B, another embodiment of the nib 1900 may comprise: a shank portion 1905, head portion 1910, face portion 1915, and collar portion 1920. The nib 1900 is preferably adapted to attach or couple to a proximal end of a front housing or distal end of a rear housing. The shank portion 1905 is preferably adapted to contact a liquid in a reservoir such that liquid may transfer from the shank portion 1905 to the head portion 1910 of the nib 1900. The face portion 1915 of the nib is preferably used to contact a surface and transfer an amount of liquid to the surface. Preferably, the porosity of the nib 1900 is calibrated based upon the desired flow rate for a specific type of application. In various embodiments, the nib 1600 may be constructed with anti-microbial material.

FIGS. 19A and 19B also show that this embodiment of the nib 1900 may comprise a shorter shank portion 1905 and a collar portion 1920 for engaging and securing the nib 1900 onto a housing. This may be accomplished by matingly engaging the collar portion 1920 with a collar of a handheld topical applicator. In other embodiments, the collar portion 1920 may engage directly with the front housing or rear housing of the handheld topical applicator. FIGS. 19A and 19B also show that the face portion 1915 of the nib 1900 may be slightly curved or rounded, and not flat.

The foregoing description of the preferred embodiments have been presented for the purposes of illustration and description. While multiple embodiments are disclosed, still other embodiments will become apparent to those skilled in the art from the above detailed description, which shows and describes illustrative embodiments. As will be realized, these embodiments are capable of modifications in various obvious aspects, all without departing from the spirit and scope of the present disclosure. Accordingly, the detailed description is to be regarded as illustrative in nature and not restrictive. Also, although not explicitly recited, one or more embodiments may be practiced in combination or conjunction with one another. Furthermore, the reference or non-reference to a particular embodiment shall not be interpreted to limit the scope protection. It is intended that the scope not be limited by this detailed description, but by the claims and the equivalents to the claims that are appended hereto.

Except as stated immediately above, nothing which has been stated or illustrated is intended or should be interpreted to cause a dedication of any component, step, feature, object, benefit, advantage, or equivalent to the public, regardless of whether it is or is not recited in the claims.

What is claimed is:

1. A handheld topical applicator, comprising:
a front housing;
a first nib;
a piston;
a biasing member; and
a reservoir;
wherein said front housing contains said reservoir;
wherein said reservoir is adapted to store a liquid;
wherein said first nib is coupled to a proximal end of said front housing and is adapted to be in fluid communication with said liquid stored in said reservoir;
wherein said piston is positioned at a distal end of said front housing;
wherein said biasing member is disposed inside said piston, such that said piston is adapted to bias towards said distal end of said front housing;
wherein said piston comprises: a first cylinder, a second cylinder, one or more first tabs, and one or more second tabs;
wherein said one or more first tabs are disposed at an outer surface of said first cylinder;
wherein said one or more second tabs are disposed at an inner surface of said second cylinder; and
wherein said one or more first tabs and said one or more second tabs are adapted to produce an audible click after a user applies pressure to said first nib against a surface, such that said applied pressure causes said one or more first tabs to contact said one or more second tabs.

2. The handheld topical applicator of claim 1, further comprising:
a main housing;
wherein said main housing comprises a central opening;
wherein said main housing substantially encloses said front housing, such that, at least a portion of said first nib protrudes through said central opening of said main housing and controllably retracts through said central opening of said main housing upon said applied pressure of said first nib onto a surface;
wherein said front housing comprises a shoulder located at an exterior of said front housing;
wherein said main housing comprises an inner flange located inside an interior of said main housing; and
wherein said shoulder is adapted to restrict said projection of said at least said portion of said first nib through said central opening of said main housing when said shoulder of said front housing contacts said inner flange of said main housing.

3. The handheld topical applicator of claim 2, wherein said one or more first tabs and one or more second tabs produce a tactile response upon receiving said applied pressure to said first nib.

4. The handheld topical applicator of claim 1, wherein said first nib is one of a plurality of nibs; and
wherein said first nib is adapted to be replaced with one or more different nibs of said plurality of nibs.

5. The handheld topical applicator of claim 4, wherein said plurality of nibs have different porosity densities, such that said handheld topical applicator is adjustable for one or more different applications.

6. The handheld topical applicator of claim 4, wherein said one or more of said plurality of nibs are constructed of an anti-microbial material.

7. The handheld topical applicator of claim 1, wherein said liquid stored in said reservoir is limited to an amount for a single use application, such that said handheld topical applicator is a single use device.

8. The handheld topical applicator of claim 1, wherein said main housing comprises a window indicator positioned outside said reservoir to show an amount of said liquid stored in said reservoir.

9. The handheld topical applicator of claim 8, wherein said front housing is constructed of a transparent material.

10. The handheld topical applicator of claim 1, wherein said first nib is adapted to change color based on an amount of said liquid stored in said reservoir.

11. The handheld topical applicator of claim 1, wherein said first nib is adapted to release a predetermined amount of liquid when said first nib is applied against a surface based on a flow rate;
wherein said flow rate is based on a material density of said reservoir and a porosity of said first nib.

12. A handheld topical applicator, comprising:
a front housing;
a first nib;
a piston;
a biasing member; and
a reservoir;
wherein said front housing contains said reservoir;
wherein said reservoir is adapted to store a liquid;
wherein said first nib is coupled to a proximal end of said front housing and is adapted to be in fluid communication with said liquid stored in said reservoir;
wherein said piston is positioned at a distal end of said front housing;
wherein said biasing member is disposed within said piston, such that said piston is adapted to bias towards said distal end of said front housing;
wherein said piston comprises: a first cylinder, a second cylinder, one or more first tabs, and one or more second tabs;
wherein said one or more first tabs are disposed at an outer surface of said first cylinder;
wherein said one or more second tabs are disposed at an inner surface of said second cylinder; and
wherein said one or more first tabs and said one or more second tabs are adapted to produce an audible click after a user applies a pressure to said first nib against a surface for a predetermined amount of time, such that said applied pressure of said first nib against said surface causes said one or more first tabs to contact said one or more second tabs.

13. The handheld topical applicator of claim 12, further comprising:
a main housing;

wherein said main housing comprises a central opening;

wherein said main housing substantially encloses said front housing, such that, at least a portion of said first nib protrudes through said central opening of said main housing and controllably retracts through said central opening of said main housing upon compression of said first nib onto a surface;

wherein said front housing comprises a shoulder located at an exterior of said front housing;

wherein said main housing comprises an inner flange located inside an interior of said main housing; and wherein said shoulder is adapted to restrict said projection of said portion of said first first nib through said central opening of said main housing when said shoulder of said front housing contacts said inner flange of said main housing.

14. The handheld topical applicator of claim 13, wherein said one or more first tabs and one or more second tabs produce a tactile response upon receiving said applied pressure to said first nib.

15. The handheld topical applicator of claim 14, wherein said first nib is one of a plurality of nibs; and
wherein said first nib is adapted to be replaced with one or more different nibs of said plurality of nibs.

16. The handheld topical applicator of claim 15, wherein said one or more different nibs have different porosity densities, such that said handheld topical applicator is used for one or more different applications.

17. The handheld topical applicator of claim 16, wherein said main housing comprises a window indicator positioned outside said reservoir;
wherein said window indicator shows an amount of said liquid stored in said reservoir.

18. The handheld topical applicator of claim 17, wherein said front housing is constructed of a transparent material.

19. The handheld topical applicator of claim 18, wherein said first nib is adapted to change color based on an amount of said liquid stored in said reservoir.

20. The handheld topical applicator of claim 12, wherein said first nib is adapted to release a predetermined amount of liquid when said first nib is applied against a surface based on a flow rate; and
wherein said flow rate is based on a material density of said reservoir and a porosity of said first nib.

* * * * *